(12) United States Patent
White et al.

(10) Patent No.: US 7,070,554 B2
(45) Date of Patent: Jul. 4, 2006

(54) BRACHYTHERAPY DEVICES AND METHODS OF USING THEM

(75) Inventors: Jack White, Alpharetta, GA (US); Stephen N. Carr, Flowery Branch, GA (US); Kyle Millage, Flemington, NJ (US)

(73) Assignee: Theragenics Corporation, Buford, GA (US)

( * ) Notice: Subject to any disclaimer, the term of this patent is extended or adjusted under 35 U.S.C. 154(b) by 117 days.

(21) Appl. No.: 10/342,536

(22) Filed: Jan. 15, 2003

(65) Prior Publication Data

US 2004/0138515 A1 Jul. 15, 2004

(51) Int. Cl.
*A61N 5/00* (2006.01)

(52) U.S. Cl. .......................................... 600/3
(58) Field of Classification Search ................ 427/5–6; 376/158, 169, 184, 186; 378/45; 600/1–8; 250/506.1, 507.1; 206/365; 976/DIG. 351
See application file for complete search history.

(56) References Cited

U.S. PATENT DOCUMENTS

| | | | | |
|---|---|---|---|---|
| 839,061 | A | * | 12/1906 | Farjas ............................. 600/3 |
| 2,517,568 | A | * | 8/1950 | Hissong ........................... 600/1 |
| 2,559,793 | A | * | 7/1951 | Pregel ............................. 600/1 |
| 3,662,882 | A | * | 5/1972 | Obermayer ..................... 378/45 |
| 3,673,411 | A | * | 6/1972 | Glasser ....................... 250/506.1 |
| 4,244,357 | A | * | 1/1981 | Morrison ......................... 600/6 |
| 4,759,345 | A | * | 7/1988 | Mistry ............................. 600/8 |
| 4,850,377 | A | | 7/1989 | Parker et al. |
| 4,996,159 | A | | 2/1991 | Glaser |
| 5,165,415 | A | | 11/1992 | Wallace et al. |
| 5,203,353 | A | | 4/1993 | Easley et al. |

(Continued)

FOREIGN PATENT DOCUMENTS

WO   WO 99/04857   2/1999

OTHER PUBLICATIONS

Paul T. Finger, MD, Anthony Berson, MD, et al., "Ophthalmic Plaque Radiotherapy for Age related Macular Degeneration Associated with Subretinal Neovascularization," *American Journal of Ophthalmology*, vol. 127,Feb. 1999,pp. 170-177.

(Continued)

*Primary Examiner*—Samuel G. Gilbert
(74) *Attorney, Agent, or Firm*—Knoble Yoshida & Dunleavy, LLC

(57) ABSTRACT

Brachytherapy devices are provided for delivering a substantially uniform dose rate of radiation to a treatment area at a predetermined treatment depth. The devices include a holder defining a cavity, and a radioactive material located within the cavity. The holder comprises radiation-shielding material therein. The holder and the radioactive material are positioned to cooperatively provide a substantially uniform dose rate of radiation to a treatment area at a predetermined treatment depth. Also disclosed are methods for treating macular degeneration or ocular melanoma. The methods involve positioning a brachytherapy device in contact with or in close proximity to tissue located in a treatment area and exposing the tissue located in the treatment area to a therapeutic dose of radiation, which is delivered at a substantially uniform dose rate over the treatment area at a predetermined treatment depth. The devices and methods of the invention also ensure that the radiation delivered outside the treatment area is substantially reduced relative to the radiation delivered within the treatment area to minimize exposure of healthy tissue to radiation. The provision of a substantially uniform dose rate in the treatment area prevents substantial over- and under-exposure to radiation of different portions of the tissue in the treatment area.

31 Claims, 20 Drawing Sheets

U.S. PATENT DOCUMENTS

| | | | |
|---|---|---|---|
| 5,342,283 A | | 8/1994 | Good |
| 5,426,662 A | | 6/1995 | Mefferd et al. |
| 5,431,907 A | | 7/1995 | Abelson et al. |
| 5,637,073 A | | 6/1997 | Freire |
| 6,030,333 A | * | 2/2000 | Sioshansi et al. ............... 600/3 |
| RE36,693 E | * | 5/2000 | Reich ...................... 250/507.1 |
| 6,075,032 A | | 6/2000 | Campochiaro et al. |
| 6,099,457 A | | 8/2000 | Good |
| 6,102,844 A | | 8/2000 | Ravins et al. |
| 6,113,529 A | * | 9/2000 | Shi ................................ 600/7 |
| 6,183,410 B1 | | 2/2001 | Jacobsen et al. |
| 6,217,503 B1 | * | 4/2001 | Weinberger et al. ........... 600/3 |
| 6,293,899 B1 | * | 9/2001 | Sioshansi et al. ............... 600/3 |
| 6,319,190 B1 | | 11/2001 | Schmidt et al. |
| 6,372,753 B1 | | 4/2002 | Campochiaro et al. |
| 6,443,881 B1 | | 9/2002 | Finger |
| 6,458,069 B1 | | 10/2002 | Tam et al. |
| 6,639,237 B1 | * | 10/2003 | Pedersen et al. ......... 250/506.1 |
| 6,666,811 B1 | * | 12/2003 | Good ............................ 600/8 |
| 6,679,824 B1 | * | 1/2004 | Reed et al. .................... 600/7 |
| 2002/0195575 A1 | * | 12/2002 | Martin .................... 250/506.1 |
| 2003/0226981 A1 | * | 12/2003 | Schmidt .................. 250/506.1 |

OTHER PUBLICATIONS

Paul T. Finger, MD, Ray Iezzi, MD, et al., "Plaque-Mounted Diode-Light Transillumination for Localization Around Intraocular Tumors," *Archives of Ophthalmology*, vol. 117, Feb. 1999, pp. 179-183.

Paul T. Finger, MD, Raylezzi, MD, et al., "Diode-Light Transillumination for Opthalmic Plaque Localization Around Juxtapapillary Choroidal Melanomas," *Int. J.Radiation Oncology Biol. Phys.*, vol. 44, No. 4, 1999, pp. 887-890.

Paul T. Finger, MD, "Radiation Therapy forChoroidal Melanoma," *Survey of Ophthalomology*, vol. 42, Nov.-Dec. 1997. pp. 215-232.

* cited by examiner

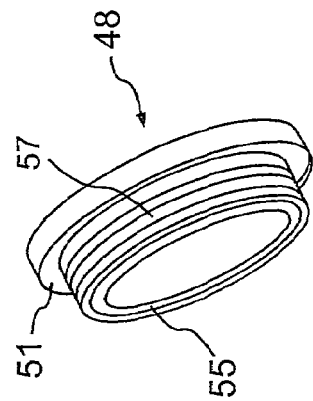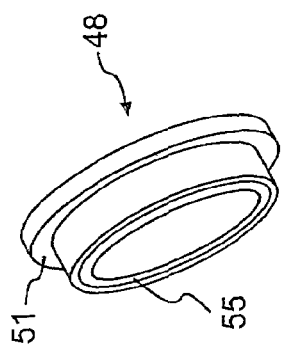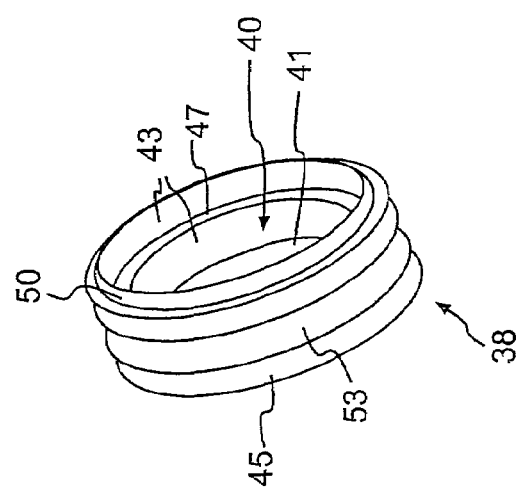

BRACHYTHERAPY DEVICES AND METHODS OF USING THEM

BACKGROUND OF THE INVENTION

1. Field of the Invention

The present invention relates to devices and methods for brachytherapy, and more particularly to devices and methods for treating macular degeneration and/or ocular melanoma using radiation therapy.

2. Description of the Related Technology

Macular degeneration is a common disease that is the leading cause of legal blindness among older people in the United States and Europe. Macular degeneration is believed to affect about 10% of those between the ages of 65 and 75 and about 30% of those between the ages of 75 and 85. Macular degeneration, wet type, is commonly caused by excessive growth of neovascular tissue to provide blood supply to oxygen-deprived retinal tissue. There is currently no known treatment for the dry type of macular degeneration. However, the neovascular tissue is very delicate and thus the blood vessels contained therein break easily, causing bleeding and damage to surrounding tissue, which often leads to macular degeneration.

Modern attempts to alleviate the effects of macular degeneration have included laser and surgical techniques. Although burning the retinal membrane with a laser has been effective in temporarily controlling the growth of neovascular tissue, the capillaries in the tissue tend to resume their growth in about three to four months following laser surgery, thereby requiring additional laser treatments until the laser treatments eventually become ineffective. Laser burning techniques are also known to destroy more cone cells, in some cases, than are destroyed by macular degeneration, which is counterproductive.

Surgery, on the other hand, has proven to be successful in removing neovascular tissue without substantially affecting the cone cell population. However, even the best surgical techniques merely postpone the growth of the vessels in the neovascular tissue for about two or three months, after which, more vessels grow into the scarred neovascular tissue and the patient must return for more surgery. Also, surgery has the disadvantage that it may cause more trauma to surrounding tissue than, for example, brachytherapy.

Radiation therapy has been attempted to treat macular degeneration. For example, U.S. Pat. No. 5,637,073 to Freire discloses a device, which is useful in treating macular degeneration. The proximal end portion of the device of Freire includes a handle and the distal end portion includes a wand having a cavity located at its distal tip to hold a radioactive material such as $^{90}$Sr. Unfortunately, the device of Freire suffers several drawbacks such as failing to provide a uniform radiation dosage to the treatment volume, which can easily result in over- or under-dosing the treatment volume. The use of $^{90}$Sr can also result in a large surface dose to the sclera immediately in contact with the applicator.

Accordingly, there is still a need for an improved radiation therapy device for providing a substantially uniform radiation dosage to the treatment area.

There is also a need for an improved radiation therapy device for the treatment of disorders such as macular degeneration and/or ocular melanoma.

There is also a need for improved methods to treat macular degeneration and/or ocular melanoma using radiation.

SUMMARY OF THE INVENTION

To fulfill these and other needs, in a first aspect, the present invention provides a brachytherapy device formed by a bottom an annular sidewall affixed at one end thereof to the bottom to define a cavity for holding a radioactive material. The device includes a radioactive material having an annular shape located within the cavity. The bottom and annular sidewall include a radiation shielding material.

In a second aspect, the present invention provides a brachytherapy device including a holder for radioactive material. The holder is formed by a bottom and an annular sidewall, which together define a cavity. A radioactive material is located within the cavity. The bottom and annular sidewall of the holder include radiation-shielding material. The shape of the holder and the shape of the radioactive material cooperate to provide a substantially uniform dose rate of radiation within a predetermined treatment area at a predetermined treatment depth.

In a third aspect, the present invention provides a brachytherapy device for eye therapy, which includes a handle, a wand attached at a proximal end thereof to the handle, and a holder located at a distal end of the wand for holding radioactive material. The holder is formed by a combination of a bottom and an annular sidewall affixed to the bottom to define a cavity. The bottom and annular sidewall of the holder include radiation-shielding material. A radioactive material is located within the cavity. The holder is sufficiently small to be inserted between the sclera and the eyelid for treatment of ocular disorders by brachytherapy.

In a fourth aspect, the invention provides a method for performing brachytherapy. The method involves the steps of positioning a brachytherapy device behind the macula and exposing tissue to a substantially uniform dose rate of radiation in a treatment area at a predetermined treatment depth.

For a better understanding of the invention, its advantages, and the objects obtained by its use, reference should be made to the drawings and to the accompanying descriptive matter, in which there are illustrated and described preferred embodiments of the present invention.

BRIEF DESCRIPTION OF THE DRAWINGS

FIG. 2C is a perspective view of the holder shown in FIGS. 2A–2B.

FIG. 2D is a perspective view of the cap shown in FIG. 2A.

FIG. 2E is a perspective view of an alternative embodiment of a cap including threads for providing a threaded fit with a holder.

DETAILED DESCRIPTION OF THE PREFERRED EMBODIMENT(S)

Figure 1:
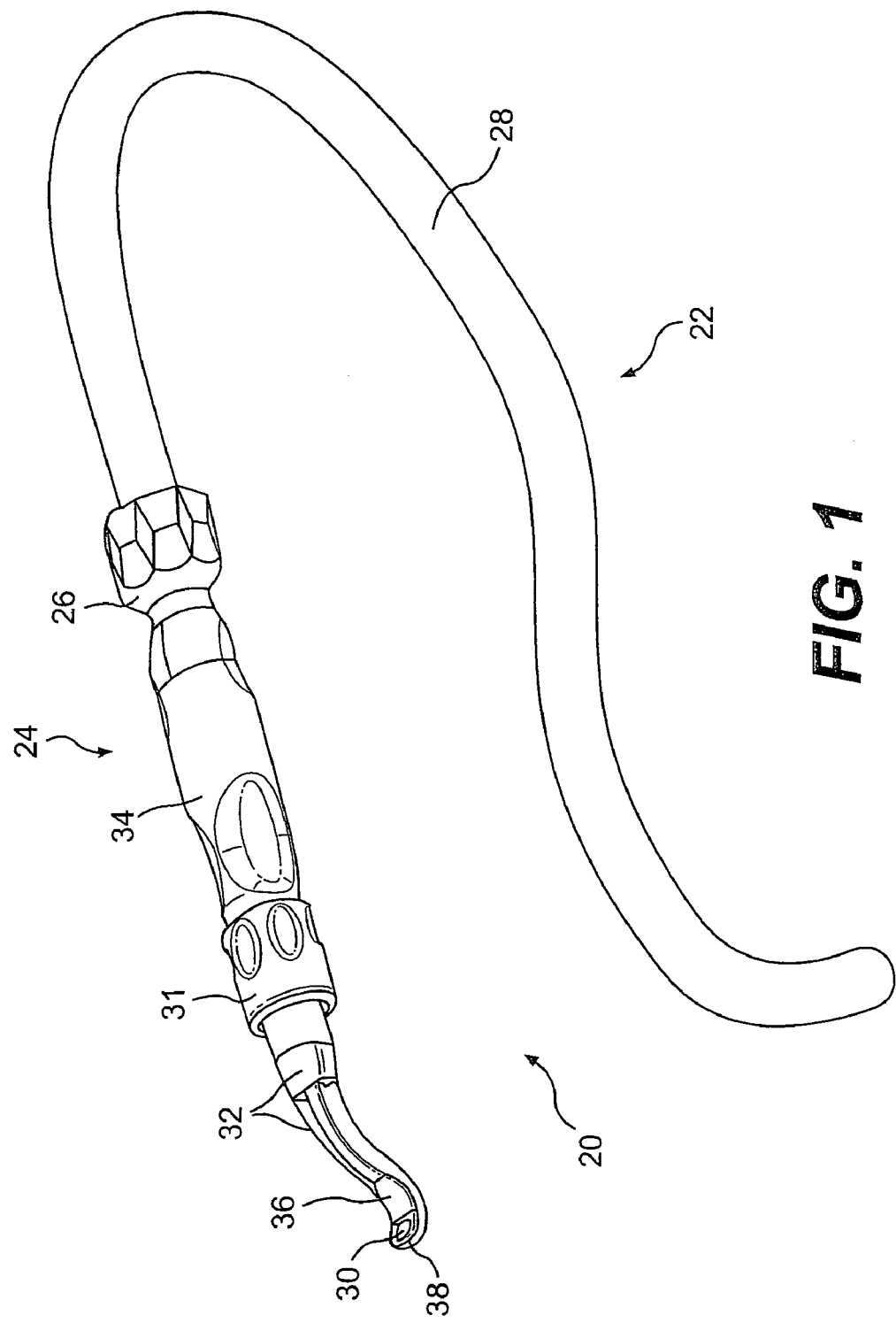
FIG. 1 is a perspective view of a brachytherapy device of the present invention.

Referring now to the drawings, wherein like reference numerals designate corresponding structure throughout the several views, and referring in particular to FIG. 1, a first embodiment of a brachytherapy device 20 for eye therapy is shown. For the purpose of description, brachytherapy device 20 is divided into a proximal portion 22 and a distal portion 24. The proximal portion 22 includes an articulating arm lock 26 for connecting the proximal portion 22 of the device 20 to the distal portion 24 of the device 20. The articulating arm lock 26 locks one end of the articulated lockable arm 28 into place. The articulated lockable arm 28 is flexible and a person or an instrument can manipulate its shape and orientation.

The distal portion 24 of the brachytherapy device 20 includes a wand 36, and a holder 38 located at the distal end of the wand 36 for housing a suitable radioactive material. The proximal end of the wand 36 is releasably connected to wand handle 34. The radioactive material is used for brachytherapy, in this case for treatment of the eye to relieve, for example, macular degeneration or ocular melanoma.

The brachytherapy device 20 may further include a removable or retractable sheath 32 covering the holder 38 and, optionally at least a portion of the wand 36. In use, the sheath 32 will cover holder 38 and, optionally, at least a portion of wand 36 during insertion of the brachytherapy device 20. The sheath 32 functions to provide a sterile contact surface between the device 20 and the patient and thus the sheath 32 is preferably a sterile sheath 32. Sheath 32 may be disposable or sterilizable to permit either sterilization of sheath 32 after each use or disposing of sheath 32 in favor of a new sterile sheath 32 after each use.

The brachytherapy device 20 may also include a retractable shield 30. Once the holder 38 of the brachytherapy device 20 is properly positioned for treatment, the retractable shield 30 can be removed or retracted to expose the radioactive material in the holder 38. Preferably, the retractable shield 30 includes a radiation shielding material in order to minimize leakage of radiation from the holder 38 when the brachytherapy device 20 is not in use. The retractable shield 30 is connected to a shield retracting mechanism 31, which is actuated to retract shield 30 and may be rotated in the opposite direction to extend shield 30 back over holder 38 at the end of treatment to shield the radioactive material during removal of the device 20 from the treatment area.

Figure 2A:
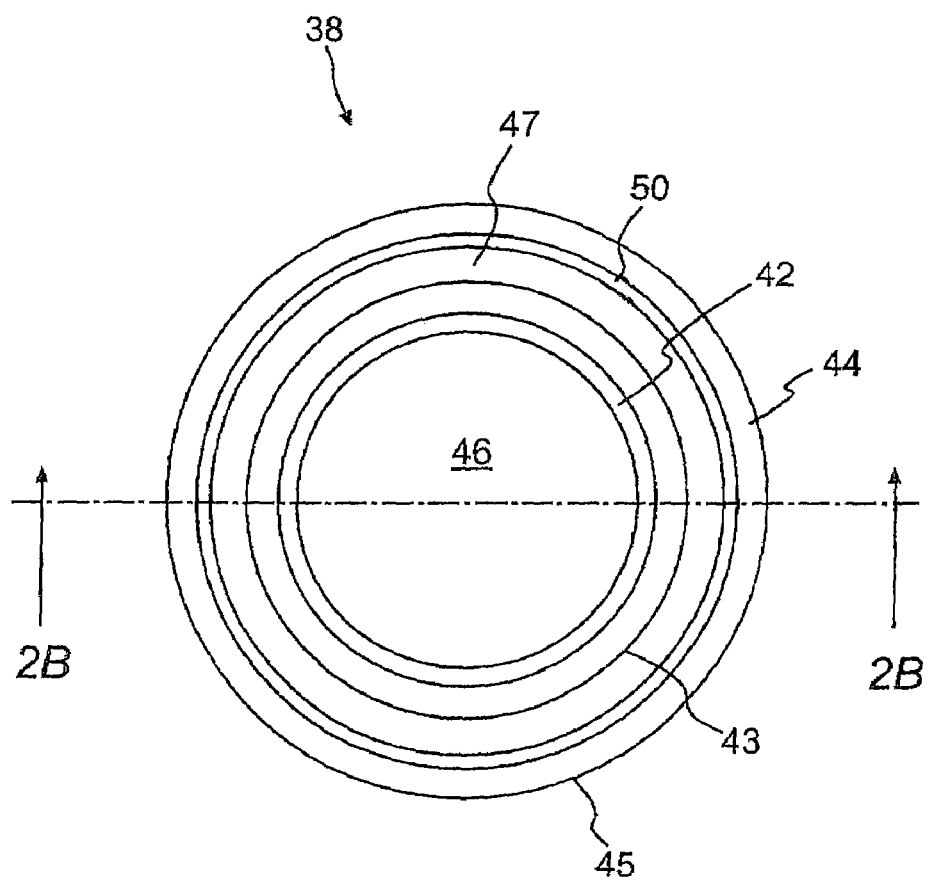
FIG. 2A is a top view of a holder for radioactive material in accordance with the present invention, shown containing a radioactive material and without a cap.
Figure 2B:
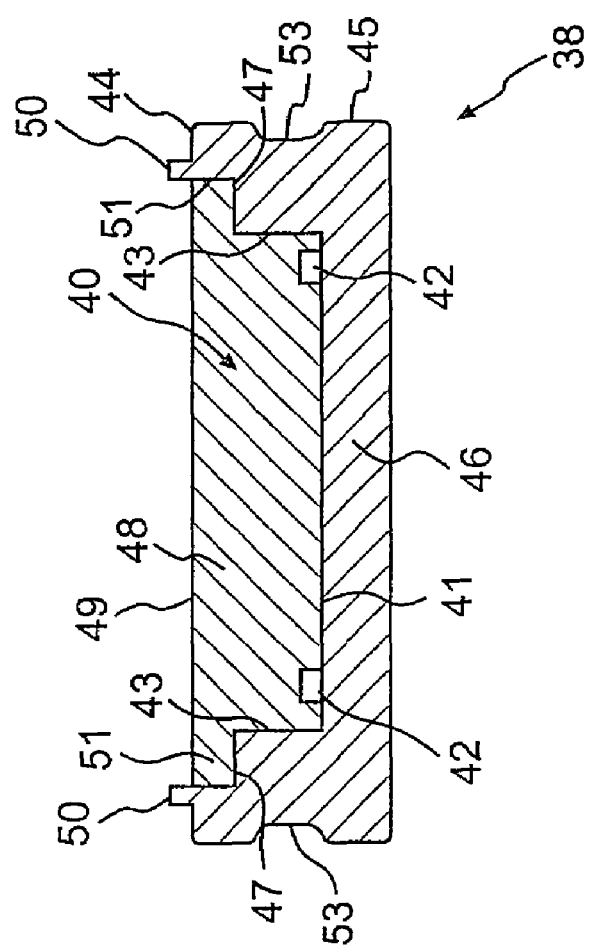
FIG. 2B is a cross-sectional view of the holder shown in FIG. 2A along line 2B—2B of FIG. 2A, with a cap inserted into the cavity in the holder.
Figure 3:
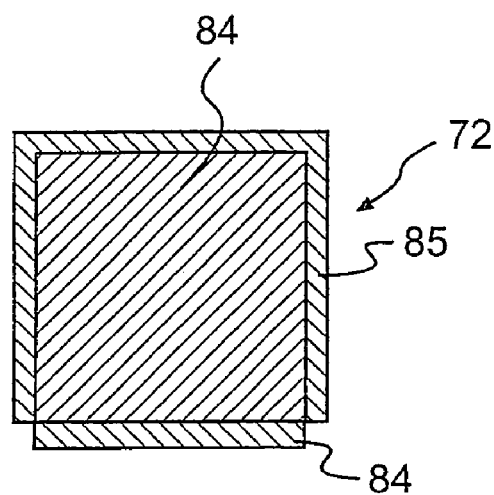
FIG. 3 is a partial cross-sectional view of an embodiment of a device containing radioactive material in accordance with the present invention.

Referring now to FIGS. 2A and 2B, holder 38 is formed by a combination of a bottom 46 and an annular sidewall 44, which is preferably sealed to, or formed integrally with, the bottom 46 at a first end of the annular sidewall 44. A second end of the annular sidewall 44 forms an opening in the holder 38 as shown in FIG. 2B. The annular sidewall has an inner surface 43 and an outer surface 45. In the embodiment shown in FIGS. 2A–2B, the annular sidewall 44 and bottom 46 define a substantially cylindrical cavity 40. Located within cavity 40 is an annular ring 42, which includes a radioactive material. Further details of the annular ring 42 are shown in FIG. 3. Annular ring 42 is located on the top surface 41 of the bottom 46 of holder 38 in the desired position.

Also shown in FIGS. 2B and 2D–2E is a cap 48, which is not shown in FIG. 2A. The cap 48 can be any shape as long as at least a portion of the cap 48 is located between the radioactive material and the opening in the holder 38. The shape of the cap 48 preferably conforms to the shape of substantially the entire remaining empty portion of cavity 40 to retain the annular ring 42 in place and fill the cavity 40 between the inner surface 43 of annular sidewall 44 and the top surface 41 of bottom 46 to form a relatively smooth upper surface 49 of cap 48 which is preferably flush with the top of the annular sidewall 44 to thereby provide a relatively smooth contact surface between the device and the patient in use. Upper surface 49 of cap 48 is located slightly below the upwardly protruding peripheral lip 50 as shown in FIG. 2B so that the peripheral lip 50 can be crimped to lock the cap 48 into place as described below. Annular sidewall 44 includes a peripheral shoulder 47 on the inner surface 43.

Cap 48 is formed with a peripheral extension 49 that is adapted to rest on peripheral shoulder 47 of annular sidewall 44 as shown in FIG. 2A. Cap 48 also serves to cover the radioactive material so that the radioactive material does not come into direct contact with the tissue of the patient or persons handling the holder 38. The annular sidewall 44 may include a device for holding cap 48 in cavity 40 such as peripheral lip 50 that may be crimped over the periphery extension 49 of the upper surface of cap 48 by pressing the peripheral lip 50 downwards and inwards toward the center of cavity 40 in order to hold cap 48 in place in cavity 40. The peripheral lip 50 may preferably be formed integrally with the annular sidewall 44 as shown in FIG. 2B. In a preferred embodiment, the annular sidewall 44, the bottom 46 and the peripheral lip 50 are formed integrally and the cap 48 is retained within the cavity 40 by a combination of a mechanical fastener such as peripheral lip 50 and the provision of a snap fit, a slip fit, a friction fit, or a threaded fit between the cap 48 and holder 38. As shown in FIG. 2B, the cap 48 fits snugly with the annular sidewall 44 to provide any of a snap fit, a slip fit or a friction fit, depending on how snugly the cap 48 fits with the annular sidewall 44. Preferably, cap 48 has a curved upper surface. More preferably, the curved upper surface of cap 48 has a radius of curvature that substantially conforms to the shape of the eye to thereby facilitate insertion of the device into the eye.

Holder 38 may also include a peripheral indentation 53 in the outer surface 45 of sidewall 44 as shown in FIGS. 2B-2C. The purpose of the peripheral indentation 53 is to attach the holder 38 to a delivery device such as a wand, filament or other delivery device via a snap-fit, molded or pressed attachment.

FIG. 2C is a perspective view of the holder 38 depicted in FIGS. 2A-2B, without cap 48 inserted therein. FIG. 2C shows further detail of the peripheral indentation 53, peripheral shoulder 47 and peripheral lip 50.

FIG. 2D is a perspective view of cap 48 depicted in FIG. 2B. FIG. 2D shows the underside of peripheral extension 51 of cap 48 designed to rest on peripheral shoulder 47 of annular sidewall 44. Also shown in FIG. 2D is the annular slot 55 in the bottom of cap 48 which is adapted to fit around annular ring 42 as shown in FIG. 2B. FIG. 2E is a perspective view of an alternative embodiment of a cap 48 which includes threads 57 for providing a threaded connection with the inner surface 43 of holder 38.

Generally, the holder 38, including the annular sidewall 44 and the bottom 46, contains a shielding material for shielding at least a substantial portion of the radiation emitted by the radioactive material contained in annular ring 42. Preferably, holder 38 is made from a metal or metal alloy such as stainless steel, gold, tungsten, lead or another suitable radiation shielding material. A suitable radiation shielding material is a material that prevents at least a substantial portion of the radiation emitted by at least one radioactive isotope contained in annular ring 42 from passing through the shielding material.

The shielding material serves to protect the user of the device and the patient from radiation during preparation and insertion of the device prior to treatment. The shielding material also participates in shaping the dose rate profile delivered by the radioactive material during treatment, as discussed in greater detail below. As a result, the shape of the holder 38 can be important in some embodiments of the present invention since it will influence the dose rate profile delivered by the radioactive material located in the holder 38.

Annular sidewalls and a round bottom form the holders shown in the figures. The cross-section of the annulus may be of any suitable shape including, but not limited to, square, rectangular, polygonal, circular, and elliptical depending on the particular shape desired for the treatment area, as well as manufacturing concerns and the desirability of having no sharp edges or corners on the device that could cause trauma when the holder 38 is inserted between the sclera and eyelid to effectuate treatment. Thus, the bottom of the holder may also take the form of any of these shapes.

The size of the holder 38 is adaptable to the particular treatment and/or patient to be treated. For example, the holder 38 must be sufficiently small to be inserted between the sclera and the eyelid. In addition, the dimensions of the holder 38 can be adapted to provide a treatment area of the desired size and shape since, to a large extent, the height and diameter of the annular sidewall 44 will determine the size and shape of the treatment area that will be irradiated by the radioactive material. In a preferred embodiment suitable for treatment of macular degeneration or ocular melanoma, the holder 38 has an inner diameter of less than about 10 mm, and a height of less than about 3 mm. For example, a suitable holder 38 may have a height of about 2–3 mm, an outer diameter of about 7–12 mm and an inner diameter of about 5–10 mm. More preferably, the device has an inner diameter of about 8 mm. The size of the holder 38 can be adjusted to accommodate the needs of a particular patient by adjusting for one or more of: the size of the eye, the spacing between the sclera and the eyelid, and the size of the area of tissue in need of brachytherapy.

The radioactive material may be selected from any suitable radioactive material for this purpose. Exemplary radioactive materials are iodine-125 and palladium-103. Preferably, the radioactive material emits a photon radiation such as x-ray radiation, gamma-ray radiation, or a combination thereof. Also, it is preferable to employ a radioactive material that is substantially free of radioactive isotopes other than the desired radioactive isotope, and substantially free of radioactive elements other than the desired radioactive element. In this manner, a more predictable dose rate profile can be obtained and the dosage of potentially harmful radiation can be minimized. Also, it is preferable to select a radioactive material that emits radiation that provides a dose rate profile that drops off steeply at a relatively short distance from the radioactive material. In this regard, palladium-103 is a preferred radioactive material since the dose rate varies by less than a factor of two across the treatment volume (i.e. at an axial distance of from 1.5–3.0 mm from the face of the device), but at an axial distance of 10 mm, the dose rate is less than 10% of the dose rate at 3 mm. Further, the device is designed such that the optic disc will receive less than 1% of the dose delivered to an axial distance of 3 mm. In this manner, the radiation dosage to healthy tissue outside the treatment area can be minimized. In an even more preferred embodiment, the radioactive material used in the invention is substantially free of other palladium isotopes. Preferably, the dose rate delivered by the radioactive material is from about 0.01–10 $Gy\text{-}min^{-1}$, more preferably from about 0.1–5 $Gy\text{-}min^{-1}$, and most preferably from about 0.5–3 $Gy\text{-}min^{-1}$. Preferably, said radioactive material has a radioactivity of about 0.1 to about 5 Ci.

In a preferred embodiment, the radioactive material further comprises a diluent. The diluent can be added to the radioactive material after it is eluted off the final purification anion exchange column. Alternatively, the diluent can be added during or prior to a purification process, if the diluent properties so allow. Suitable diluents for the radioactive material are known to persons skill in the art, and may include palladium metal, rhodium metal, one or more of the various substrate materials listed above, or any other suitable material which is compatible with the radiation released by the radioactive material. More preferred diluents are biocompatible materials. For example, preferred diluents for carrier-free palladium are rhodium and palladium metals, usually in the form of a soluble metal salt such as $PdCl_2$. Because palladium metal will have the same affinity for an anion exchange column as the Pd-103, it can be added as a diluent prior to a purification step employing an anion exchange column and can be co-purified along with the radioactive Pd-103.

Other preferred diluents are certain polymeric materials which can be employed as a diluent by, for example, homogeneously mixing the radioactive material with the polymer prior to its application to the substrate, or even by carrying out such mixing and using the mixture of polymeric material and radioactive material as the substrate itself.

Although the diluent may normally be considered an undesirable additive in a low energy emitting radiation source due to self-shielding effects, its addition in accordance with the present invention has been found to be advantageous in several respects, which, in some applications, may make use of such a diluent desirable. Foremost, the added diluent can serve to promote strong adhesion of the radioactive material to the substrate, thereby forming a substantially inert layer which will not allow the radioactive material to be mobilized.

Secondly, the addition of diluent provides the ability to adjust the specific activity of the radioactive material. This adjustment can be employed to provide an accurately determined desired level of therapeutic or apparent activity, as well as to compensate for the self-shielding effects of the diluent. Thirdly, if purification of the radioactive material is necessary, the presence of the diluent can, in some instances, reduce the loss of radioactive material occurring during the purification process.

The amount of diluent added, therefore, will vary depending principally upon the amount of, and specific activity of the radioactive material employed. Preferably, from about 0.1 mcg to about 100 mcg of diluent per millicurie of radioactive source material can be used. More preferably, from about 1 mcg to about 50 mcg of diluent per millicurie of radioactive source material is employed. Such amounts of diluent can ensure uniformity of the radioactive material in the radiation delivery device and can promote adherence of the radioactive material to the substrate. The term "specific activity" as used herein and in the appended claims means the total activity of the radioactive material per gram of the radioactive material.

If design considerations, e.g., the desired mass or therapeutic activity of the delivery device, so allow, nuclear reactor produced material can be added as a diluent to cyclotron-produced material and vice versa. Such addition may be employed, for example, to adjust the therapeutic activity of the radiation delivery device or to reduce the overall cost of the device.

Preferably, the cap 48 is made from a material that can partially shield low energy beta particles and ultra-low energy x-rays, while transmitting photon radiation of a therapeutically desirable energy to the treatment area. In this manner, the cap 48 can minimize the surface dose and any excessive dose gradient caused by undesirable radiation. Another function of the cap 48 is to space the radioactive material from the treatment area. This spacing also serves to reduce the amount of undesirable radiation, such as ultra-low energy x-rays, that reach the treatment area. A suitable thickness of the cap 48, when palladium-103 is employed as the radioactive material, may be anywhere from 0.25–2.0 millimeters and, more preferably, 0.75–1.5 millimeters, in order to provide the desired spacing. A further function of the cap 48 is to seal the annular ring 42 in cavity 40. The cap 48 may be made from any suitable substrate material as described below. Preferably, the cap 48 is made from a polymer such as polysulfone.

FIG. 3 depicts a partial cross-sectional view of an embodiment of an annular ring 72 including radioactive material. The annular ring 72 has for its primary function to provide a suitable substrate for retaining the radioactive material in position in the holder 38 and to shape the radioactive material to the proper shape to provide the desired dose rate profile of the radiation emitted by the radioactive material. Although use of an annular ring 72 is not absolutely necessary, it is generally desirable since the amount of radioactive material required to provide the desired dose rate profile is usually quite small. As a result, it is preferable to employ a substrate, such as annular ring 72 to permit distribution of the radioactive material over a suitable area. If no substrate or annular ring is employed, the radioactive material can be located directly in the cavity 40 in holder 38 or can be distributed in the desired shape within the cap 48. Alternatively, the radioactive material may be adhered to or incorporated in a substrate and the substrate and radioactive material together may be located within the cap 48.

A particularly preferred form of annular ring 72 is shown in partial cross-section FIG. 3. In this embodiment, the annular ring 72 is formed from a combination of substrate ring 82, a masking material 84 and a layer 85 of radioactive material. The masking material 84 functions to prevent adherence of radioactive material onto the surface of the substrate ring 82 which forms the interface between the substrate ring 82 and the masking material 84. Thus, the substrate ring 82 shown in FIG. 3 has a layer 85 of a suitable radioactive material on all of its outer surfaces except for the interface between the substrate ring 82 and the masking material 84. In an alternative, more preferred embodiment, the layer 85 of radioactive material is preferably only on the upper surface of the substrate ring 82. The annular ring 72 is placed in the bottom of cavity 40 in holder 38.

The substrate may be formed from any suitable substrate material to which the radioactive material can be adhered or within which the radioactive material can be distributed. If the radioactive material is to be distributed within the substrate, then the substrate should be made of a radiation transmitting material. The substrate can be formed from a metallic, non-metallic, polymeric, or ceramic material. Further, the substrate can be rigid, flexible, deformable, solid, hollow, or porous.

In one embodiment, the substrate is a metallic material, preferably a high atomic number metal or alloy such as metals or alloys including stainless steel, iridium, platinum, gold, tantalum, tungsten, lead. Additionally, lower atomic weight metals may also be used. These lower atomic weight metals include, but are not limited to, metals and alloys including aluminum, molybdenum, indium, lithium, silver and copper. Alloys of low-atomic weight and combinations of high and low-atomic weight metals may also be used. Alternatively, the substrate can be non-metallic, for instance it may include, carbon, diamond, or graphite. Of these substrates, gold is particularly preferred.

In another embodiment, the substrate can be formed from a biocompatible polymeric material. The polymeric material is preferably selected from the group consisting of polyvinyl chloride, polysulfones, cellulose esters, nylon, Dacron™, polyesters, polyolefins, polyurethanes, polyamides, polyimides and modified versions of one or more of these materials, as well as any other polymeric materials known by a skilled person to be suitable for this purpose. Of these substrates, polysulfones are particularly preferred.

Radiation can cause degradation of certain polymeric materials, as is known in the art. Particularly preferred polymeric materials for forming the substrate are polymeric materials which are resistant to such degradation due to exposure to radiation, such as the radiation stabilized polypropylene materials disclosed in U.S. Pat. Nos. 5,122,593 and 5,140,073, the disclosures of which patents are hereby incorporated by reference to the extent that they relate to radiation stabilized polymeric materials suitable for use as substrates in the present invention.

Optionally, the polymeric materials forming the substrate can include one or more additives to enhance the adherence of the radioactive material to the substrate. Examples of such additives include absorbent materials such as activated carbon powder, activated charcoal, and ion exchange resins. Suitable ion exchange resins include sulfonated polystyrene resins, methylene-sulfonic phenolic resins, phosphoric polystyrene resins, polystyrene resins containing quaternary ammonium groups, pyridinium polystyrene resins, epoxypolyamine resins containing tertiary and quaternary ammonium groups, acrylic resins, iminodiacetic polystyrene resins, and polystyrene resins containing polyamine groups, as well as other ion exchange resins known to persons skilled in the art.

In yet another embodiment, the substrate can be formed from a biodegradable polymeric material such as polyethylene glycol or polyethylene glycol-polyethylene oxide block copolymer. A particularly preferred substrate is made from a flexible or deformable material such as an elastomer, gel, foam or other suitable, flexible polymeric material. Exemplary, but not limiting, polymeric materials include polyurethanes, silicones and elastomers, gels or foams of polyurethanes and silicones. These materials should be suitable for adherence of a radioactive material thereto and they should exhibit good radiation stability.

The radioactive material can be applied to the outer surface of the substrate or be incorporated into the substrate. Particularly preferred methods for applying the radioactive material onto the surface of the substrate include electroless plating, electroplating, sputtering, and ion implantation including ion exchange processes, physical vapor deposition or chemical vapor deposition ("CVD"). Other processes for associating a radioactive source material with a substrate known to persons skilled in the art may also be employed.

Electroless plating of the radioactive material onto a substrate has the advantage that the process is applicable to a wide variety of substrates and is particularly useful for applying radioactive source material to non-conductive substrates. The electroless plating process has the additional advantages that there is very little loss of expensive radioactive material during the process and that a substantially uniform coating can be applied to a substrate in a relatively short time period. Also, the electroless plating process can be employed to apply a conductive coating onto a non-conductive substrate as a pretreatment of the substrate to prepare it for a subsequent electroplating step. Processes for electroplating radioactive material onto various electroconductive substrates are known to persons skilled in the art from U.S. Pat. No. 5,405,309, the disclosure of which is incorporated by reference for the purpose of describing the details of a suitable electroplating process.

Alternatively, the radioactive material can be uniformly mixed with a diluent and then coated onto the outer surface of the substrate. Suitable diluents for this purpose include those described above as well as the substrate materials described above which may be used in polymer masterbatching processes, for example. Preferred diluents are adhesives and polymeric materials such as, for example, urethanes, acrylics, chloroprenes, polyvinylalcohols, polyvinylchorides, nylons, or the like. It is preferred that the radioactive material be in solution when a diluent is used.

In embodiments where the radioactive material is incorporated directly into the substrate, this can be accomplished, for example, using ion implantation or by physically mixing the radioactive material with the substrate material and then forming the substrate from the mixture. For instance, the radioactive material can be uniformly mixed with a polymeric powder and be incorporated into the polymer matrix upon polymerization to form the substrate. Such a process is also applicable and particularly preferred when employing elastomer, foam or gel substrates. In a more preferred process, the radioactive material is mixed with a polymeric material and subsequently coated, plated or otherwise adhered to the outer surface of the substrate to form an outer, radioactive layer. This delivery device has the advantages that the radioactive material is firmly held in place in the polymer matrix, while at the same time the bulk of the radioactive material is located close to the surface of the substrate to thereby minimize self-shielding effects. Alternatively, the radioactive material may be mixed with a metallic powder of one of the various metals or alloys mentioned above for use as a substrate.

In certain preferred embodiments of the present invention, the radioactive material may be applied to the outer surface of polymer pellets, microspheres, powders or other similar materials and then the solid polymers containing radioactive source material may be physically mixed with a substrate material as described above. These embodiments are similar to polymer masterbatching techniques known to skilled persons for the purpose of incorporating various additives into polymeric materials.

The radioactive material can be supplied to above-described incorporation processes as a solid or in solution, as may be appropriate for the particular incorporation process. If supplied as a solid, the radioactive material can be a powder, or a mixture of radioactive material and a suitable solid diluent. Alternatively, the radioactive material may be supplied as solid reactor grade radioactive material or as a solid form of enriched material, which may later be activated to a suitable radioactive material, in situ.

If supplied as a solution, the radioactive material can be in the form of, for example, an amine complex obtained directly from a purification process. Alternatively, enriched material or radioactive material can be dissolved in an appropriate solvent to obtain a desired solution for a particular incorporation process. Suitable solvents for these materials are known in the art.

The substrate is shown in FIG. 3 in the form of an annular substrate ring 82. However, the substrate may take on many different forms, depending on the dose rate profile that is desired. For brachytherapy treatment of macular degeneration or ocular melanoma, the annular substrate ring 82 shown in FIG. 3, together with the design of holder 38, provide an advantageous dose rate profile as is explained further below. However, numerous other configurations of the substrate are possible. An alternative substrate is shown, for example, in FIG. 4A.

Figure 4A:
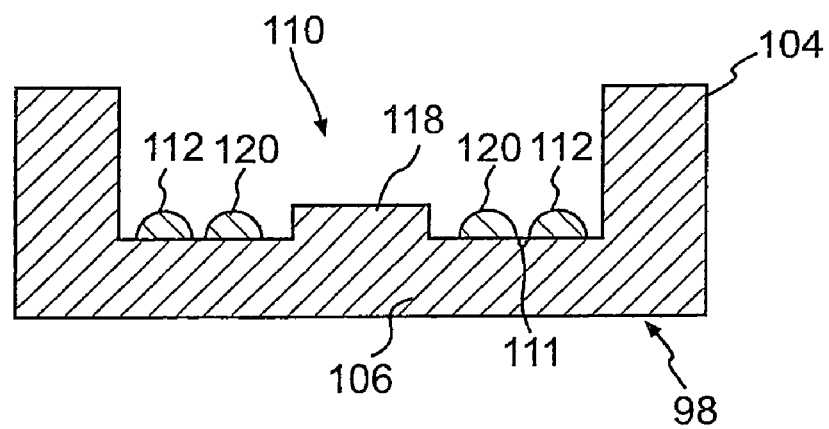
FIG. 4A is a cross-sectional view of an alternate embodiment of a holder for radioactive material in accordance with the present invention shown containing a radioactive material.

FIG. 4A is a cross-sectional view of a third embodiment of a holder 98. The holder 98 of FIG. 4A has a generally round shape and is formed by an annular sidewall 104 and a round bottom 106 to thereby define a generally cylindrical cavity 110. The round bottom 106 of the embodiment of FIG. 4A includes a raised protrusion 118 that is centrally located relative to bottom 106. The raised protrusion 118 is preferably formed integrally with the bottom 106 of the holder 98 and thus preferably contains radiation-shielding material. The purpose of the raised protrusion 118 is to block radiation from one section of the annular radioactive material from crossing over and combining with radiation from another section of the annular radioactive material. In this manner, some additional flattening of at least the central portion of the dose rate profile of the radiation emitted by the device is provided.

The embodiment of FIG. 4A includes an annular ring 112 provided with radioactive material and is positioned on the top surface 111 of the bottom 106. In addition, an illumination device 120, preferably having an annular shape is also positioned on the top surface 111 of the bottom 106 in this embodiment. The illumination device 120 may preferably be concentric with the annular ring 112. Preferably, the illumination device 120 includes a fluorescent material, which emits fluorescence upon being irradiated by radiation such as that emitted by the radioactive material used for the treatment. In this manner, the fluorescent material may serve as a marker in order to correctly position the holder 98 relative to the treatment area. Alternatively, illumination can be provided by another conventional light source such as fiber optics or light pipes.

Figure 4B:
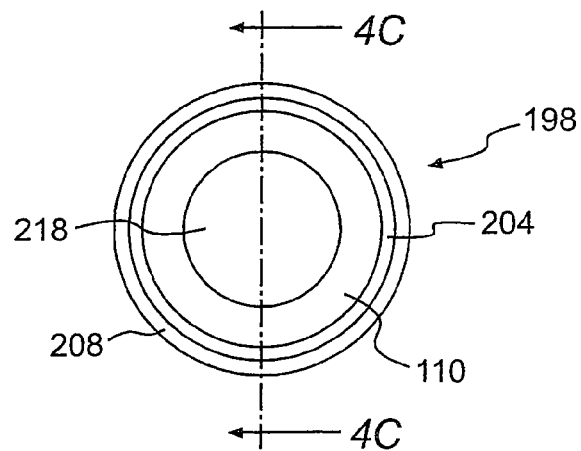
FIG. 4B is a top view of another embodiment of a holder for radioactive material in accordance with the present invention.
Figure 4C:
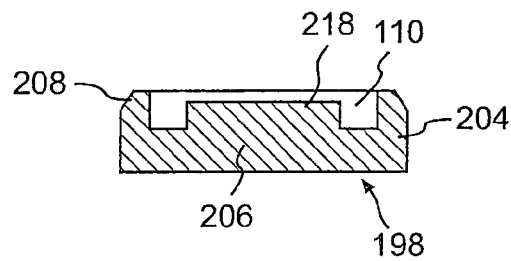
FIG. 4C is a cross-sectional view of the holder of FIG. 4B taken along the line 4C—4C of FIG. 4B.

Another embodiment of a holder 198 is shown in FIGS. 4B–4C. Holder 198 includes an annular sidewall 204 and a round bottom 206 to thereby define a generally cylindrical cavity 210. The round bottom 206 includes a raised protrusion 218 that is centrally located relative to the bottom 206. The embodiment of FIGS. 4B–4C includes an annular shoulder 208 located on annular sidewall 204. Annular shoulder 208 can be used to provide a snap or friction fit between the holder 198 and the brachytherapy device of the present invention.

Figure 5:
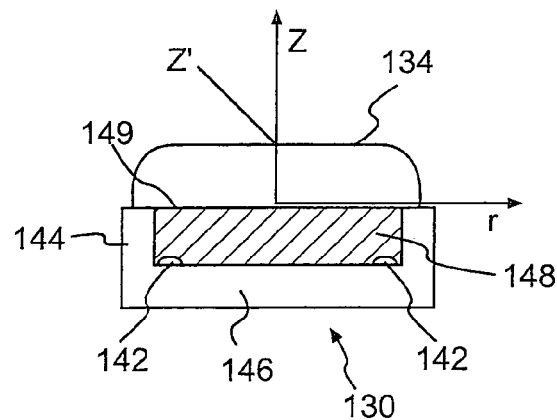
FIG. 5 illustrates a dose rate profile of a brachytherapy device in accordance with the present invention.

A feature of the brachytherapy device 130 of the present invention, as shown in FIG. 5, is that the dose rate profile provided by the brachytherapy device 130 may be shaped so as to be substantially uniform in a predetermined treatment area. FIG. 5 illustrates an exemplary radiation dose rate profile 134 of a brachytherapy device 130. In FIG. 5, the z-axis represents the axial distance from the upper surface 149 of the cap 148 of the brachytherapy device 130. The upper surface 149 of the cap 148 is positioned closest to the holder of the brachytherapy device 130 to the treatment area. The distance along the z-axis may also be referred to as the treatment depth or prescription depth. FIG. 5 also shows the r-axis, which represents the radial distance from the center of the radioactive material. In this particular example, the dose rate profile 134 represents the dose rate that is delivered by the radioactive material in the treatment area. As can be seen from FIG. 5, the dose rate at a given treatment depth $z^1$ is substantially uniform within a certain radius from the center of the radioactive material. This area of substantially uniform dose rate is a function of a combination of the shielding of the bottom 146 and annular sidewall 144 and the shape of the radioactive material provided in the annular ring 142. This type of dose rate profile 134 is advantageous because a substantially uniform radiation dose rate profile 134 will result in a substantially uniform radiation dosage being delivered over the treatment period to the tissue being treated. Therefore, over-radiation at one area and under-radiation at another area can be minimized.

The horizontal cross-section of the radioactive material may have any suitable shape including, but not limited to, square, rectangular, polygonal, circular, and elliptical depending on the particular shape desired for the treatment area and the particular dose rate profile desired. The advantage of an annular shape is that by removal of the central portion of the annulus, the dose rate profile delivered by the radioactive material is substantially flattened out over the treatment area at a given axial distance. Thus, the shape of the radioactive material contributes to the provision of a substantially uniform dose rate profile. Of course, more complex shapes of the radioactive material may be employed, such as concentric annular rings, in order to further shape the dose rate profile.

Another feature of the dose rate profile 134 of the brachytherapy device 130 is that the dose rate is substantially reduced outside the treatment area. The reduction of the radiation dose rate at this location is provided by the radiation shielding effects of the sidewall 144 and the bottom 146 of the holder 130, as well as the shape of the radioactive material in the device 130. In addition, the crimped peripheral edge 50, shown in FIG. 2B, may also contribute to the shaping of the dose rate profile if peripheral edge 50 includes a radiation shielding material. The radius of the holder 130 and the height of the sidewall 144 may be selected based on the desired size of the treatment area.

In the context of the present application, a "substantially uniform" dose rate profile refers to the provision of a dose rate profile wherein the dose rate varies by no more than 25% from the prescribed dose rate in the treatment area, measured at a particular axial distance or treatment depth. Preferably, the device of the present invention provides a dose rate over a predetermined treatment area at a constant axial distance or treatment depth that varies by not more than 25%, more preferably, the dose rate varies by not more than 15%, and most preferably, the dose rate varies by not more than 10%, with all percentage variances being calculated based on the average dose rate over the treatment area measured at a constant axial distance or treatment depth.

A dose rate is considered to be substantially reduced if the dose rate at a particular axial distance or treatment depth drops by more than 33% over a radial distance of one radius of the treatment area. Preferably, the dose rate drops off outside the treatment area by at least 50% over a distance of one radius, more preferably, at least 70%, and most preferably at least 80%, over a radial distance from the outer edge of the treatment area of one radius of the treatment area. Also, the dose rate at a radial distance from the outer edge of the treatment area of not more than two radii of the treatment area and at a predetermined treatment depth is at least 60% less than the prescribed dose at said treatment depth, and more preferably at least 75% less than the prescribed dose at said treatment depth.

Figure 6:
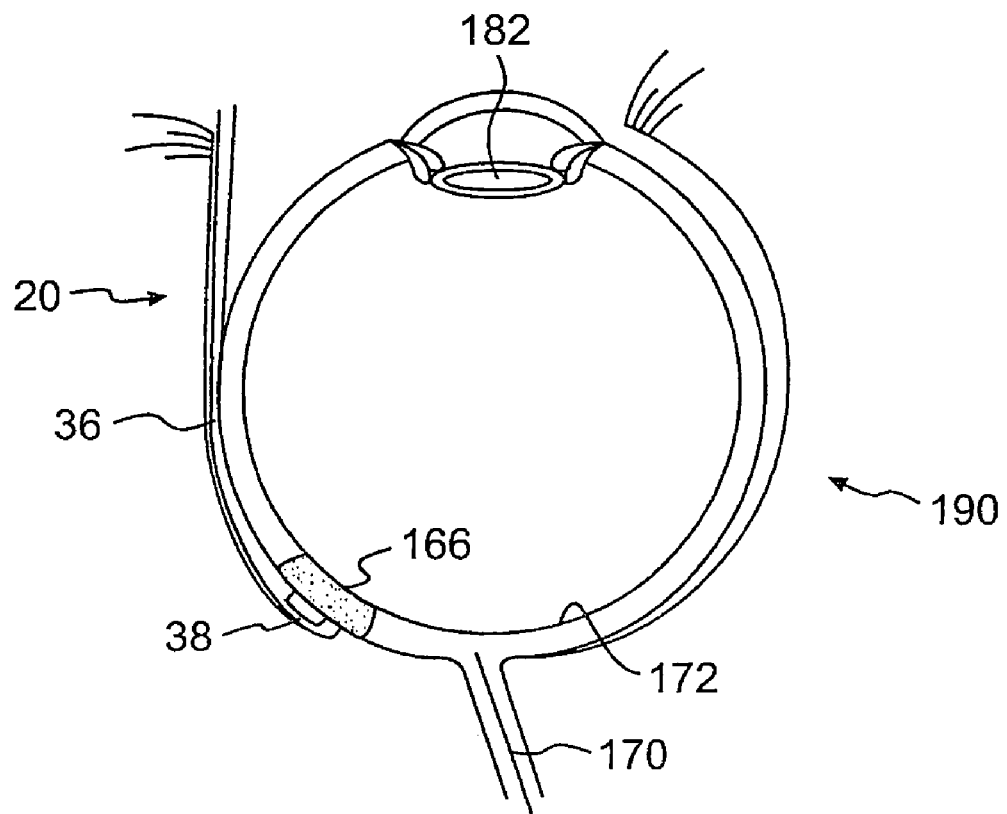
FIG. 6 illustrates a procedure for using a brachytherapy device to treat macular degeneration in accordance with the present invention.

With reference to FIG. 6, the preferred method of using the brachytherapy device of the present invention to treat macular degeneration will now be described. In a preferred embodiment, the delivery of radiation to the diseased tissue need not take more than 30 minutes, and preferably the treatment time is less than 10 minutes. The patient is briefly anesthetized during the procedure, a small incision is made in the temporal side of the conjunctiva, and the holder 38 of the brachytherapy device 20 is inserted between the sclera and the eyelid and behind the eye 190. The tissue to be treated 166 of the retina 172 may be located by shining light on the retina 172. The holder 38 is then positioned in contact with, or in close proximity to the tissue to be treated 166, preferably by tracking an illumination device located in the holder 38. The illumination device may be a plurality of fiber optic or light pipe illumination points that can be tracked, for example, by ophthalmoscopy. The location of the device can also be verified by ultrasound.

A preferred position is directly on the sclera at the base of the optic nerve, which places the device directly behind the macula. Upon proper positioning the holder 38, a retractable shield 30, preferably made of gold, is slid into an open position so as to expose the neovascular membrane in the tissue 166 to the effects of the radioactive material. One of the preferred illumination points is preferably located proximal to the active source and thus will only become visible when the retractable shield 30 is fully closed or fully open. Alternatively, the illumination point can be located such that it is only visible when the retractable shield 30 is fully open. This provides feedback to the physician that the retractable shield 30 has been fully retracted and therapy has been initiated over the entire desired treatment area. The device is then left in place for 5–30 minutes, depending on the activity of the device and the desired prescription dose.

During treatment the physician can monitor the therapy to ensure that the device is maintained in the proper position. Employing an ophthalmascope connected to a camera and a monitor for this purpose can reduce the physician's dose. After the dose has been delivered, the retractable shield 30 is closed and the device is removed. The disposable sheath can then be removed and discarded and the device returned to a shielded container for storage.

Radiation has been shown to cause endothelial cell loss, thereby causing capillary vessel closure. Further radiation prevents endothelial cell proliferation and therefore inhibits new capillary growth. The closure of the neovascular capillaries will reverse, or at least deter, the growth of the distorted retinal tissue. Also, the treatment helps to reduce fluid leakage that frequently results from sub-retinal neovascularization. If a sufficient reduction of the neovascular membrane is accomplished, the fovea can be regenerated, or at least retained, and the cone cells of the macular tissue can be preserved for the patient. It is important to note that as a result of the special dose rate profile delivered by the brachytherapy device 20 of the present invention, the lens 182, optic nerve 170 and disc of the patient's eye 190, shown in FIG. 4, are not significantly adversely affected by the treatment. It is envisioned that this procedure can substantially control or reduce the propagation of macular degeneration.

Ocular melanoma can be treated using a method similar to that described above using the brachytherapy device 20 of the present invention except that the target tissue being treated is the cancerous tissue that causes ocular melanoma. Upon treatment, growth of the cancerous tissue may be reduced or stopped.

Preferably, during the step of exposing the tissue to a therapeutic dose of radiation, the holder is positioned in contact with the tissue to be treated. As a result, it is desirable to have a smooth contact surface between the holder and the tissue to minimize potential mechanical damage to the tissue from contact with the holder. However, it is not absolutely necessary to position the holder in direct contact with the tissue and, in some instances, it may be desirable to position the holder in close proximity to the tissue rather than in direct contact therewith. In such circumstances, the holder should be placed close enough to the tissue to be treated that a therapeutic dose of radiation can be delivered to the treatment area at a predetermined treatment depth in a reasonable treatment time. Generally, the device is positioned against the sclera and the dose is shaped based on a prescription point that is located about 2 mm inside the sclera. A reasonable treatment time can, in some unusual circumstances, but generally should not, exceed about 30 minutes due to considerations of use of anesthesia and patient discomfort.

Figure 7:
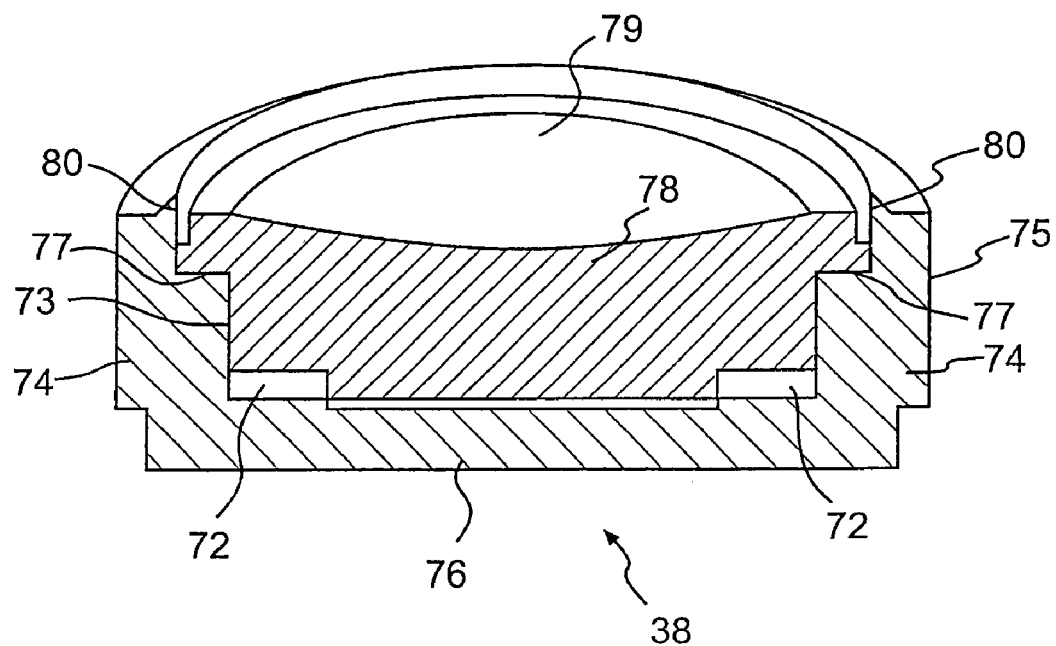
FIG. 7 illustrates a perspective view of an alternative embodiment of a holder in accordance with the present invention shown in partial cross-section.

FIG. 7 shows, in partial cross-section, an alternate embodiment of a holder 38 in accordance with the present invention. Holder 38 is formed by a combination of a bottom 76 and an annular sidewall 74, which is preferably sealed to, or formed integrally with, the bottom 76 at a first end of the annular sidewall 74. A second end of the annular sidewall 74 forms an opening in the holder 38 as shown in FIG. 7. The annular sidewall has an inner surface 73 and an outer surface 75. In the embodiment shown in FIG. 7, the annular sidewall 74 and bottom 76 define a substantially cylindrical cavity. Located within cavity 80 is an annular ring 72, which includes a radioactive material, and a cap 78. Further details of the annular ring 72 are shown in FIG. 3. Annular ring 72 is located on the top surface 71 of the bottom 76 of holder 38 in the desired position. Upper surface 79 of cap 78 is located slightly below the upwardly protruding peripheral lip 80 as shown in FIG. 2B so that the peripheral lip 80 can be crimped to lock the cap 78 into place as described below. Annular sidewall 74 includes a peripheral shoulder 77 on the inner surface 73.

Figure 8:
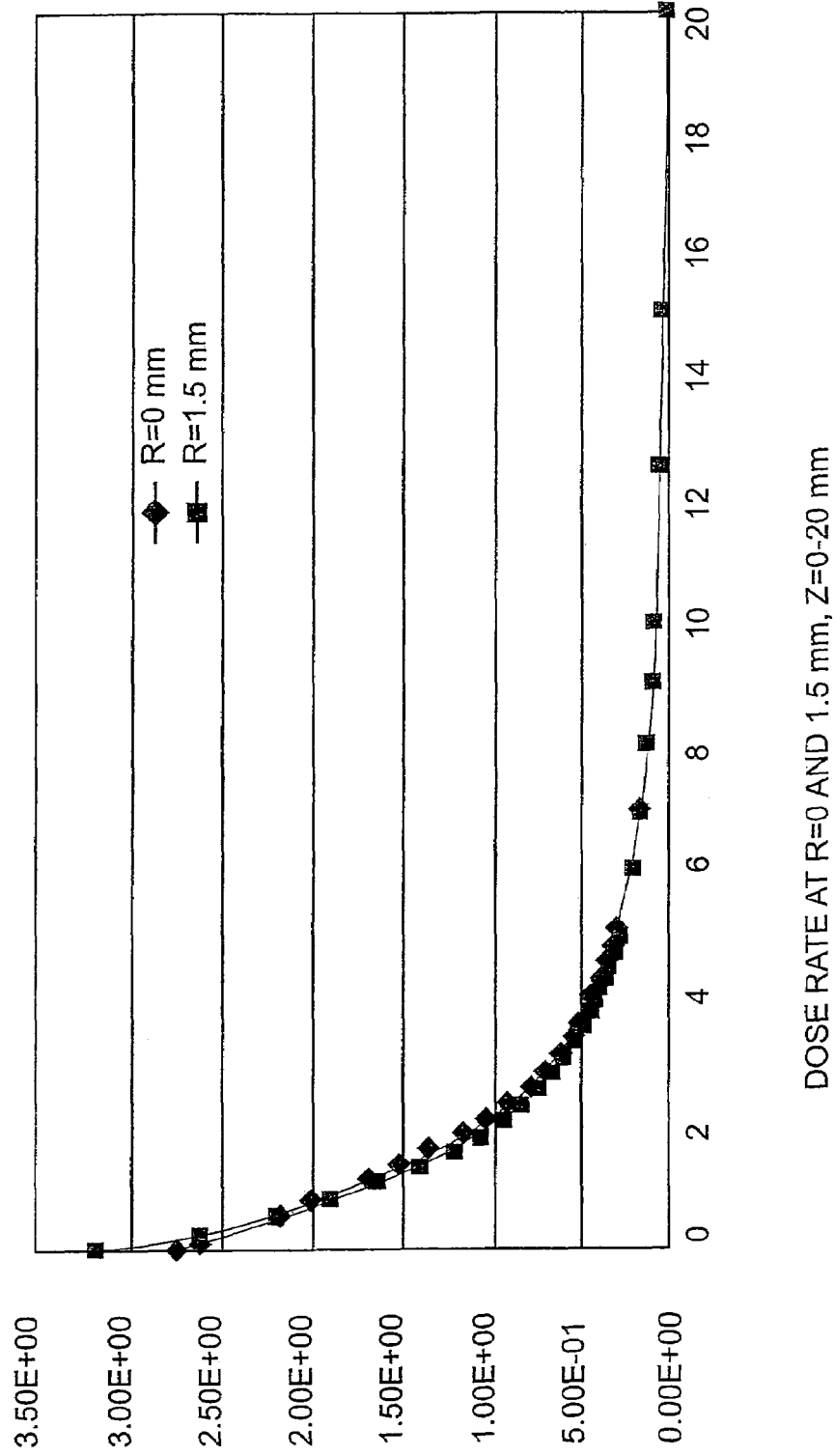
FIG. 8 exemplifies a dose rate profile of a brachytherapy device in accordance with the present invention at points where the radial distances (r), as defined in FIG. 5, are 0 mm and 1.5 mm, respectively and the axial distance (z), as defined in FIG. 5, is 0–20 mm.
Figure 9:
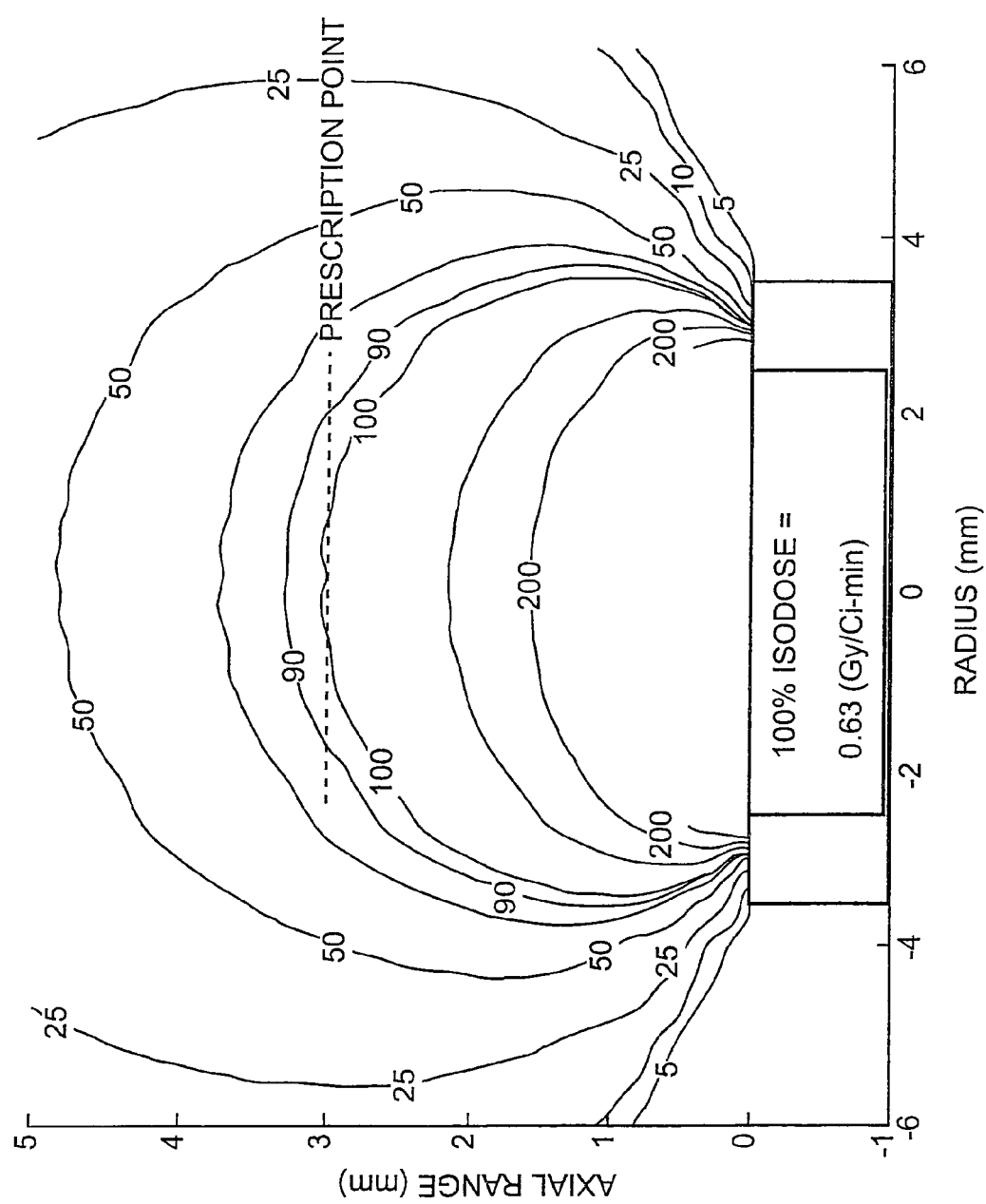
FIG. 9 is a plot of the isodose curves of a brachytherapy device according to the present invention.
Figure 10:
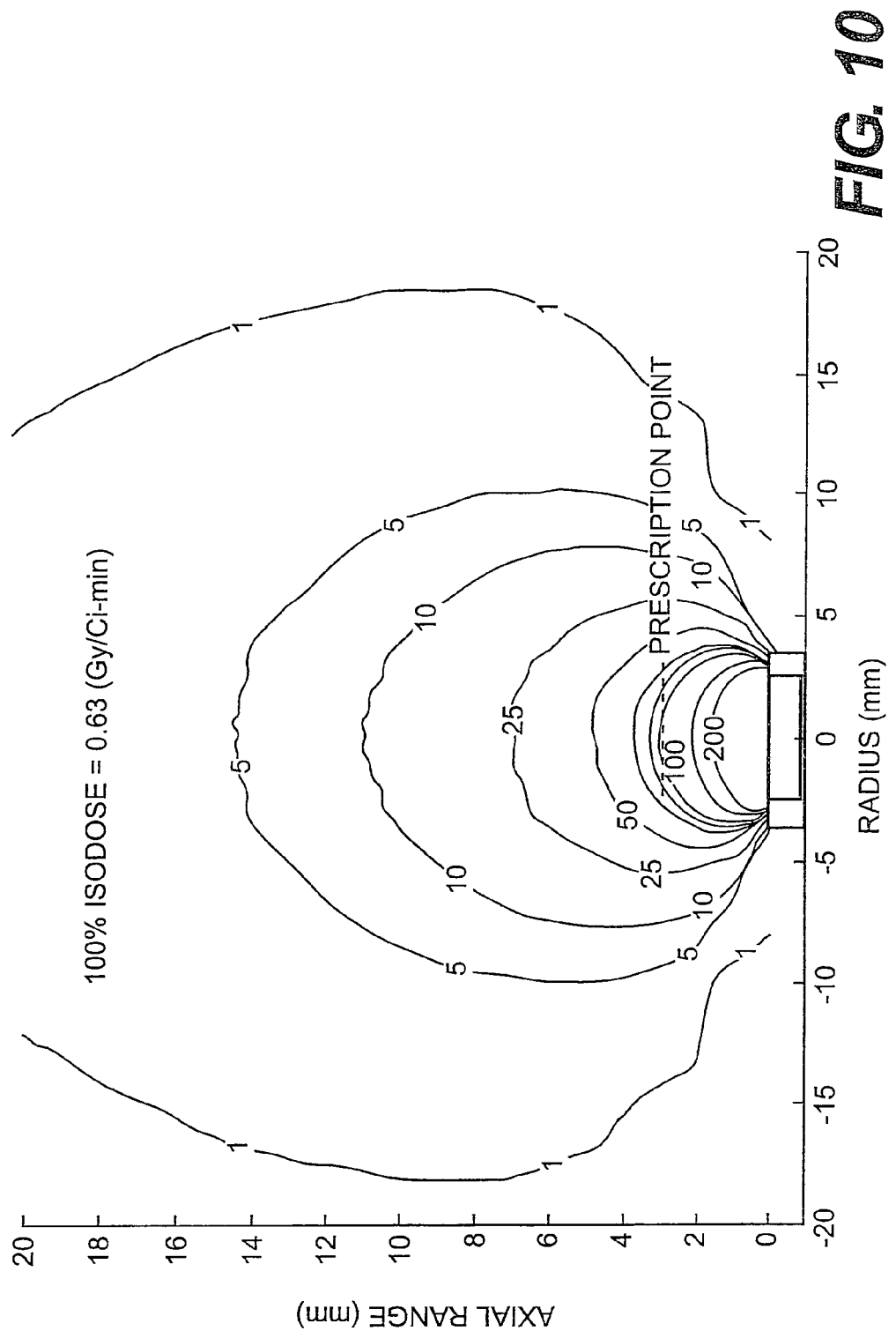
FIG. 10 is a plot of the isodose curves of a brachytherapy device according to the present invention with a wider axial and radial range than the device used to generate the plot of FIG. 9.
Figure 11:
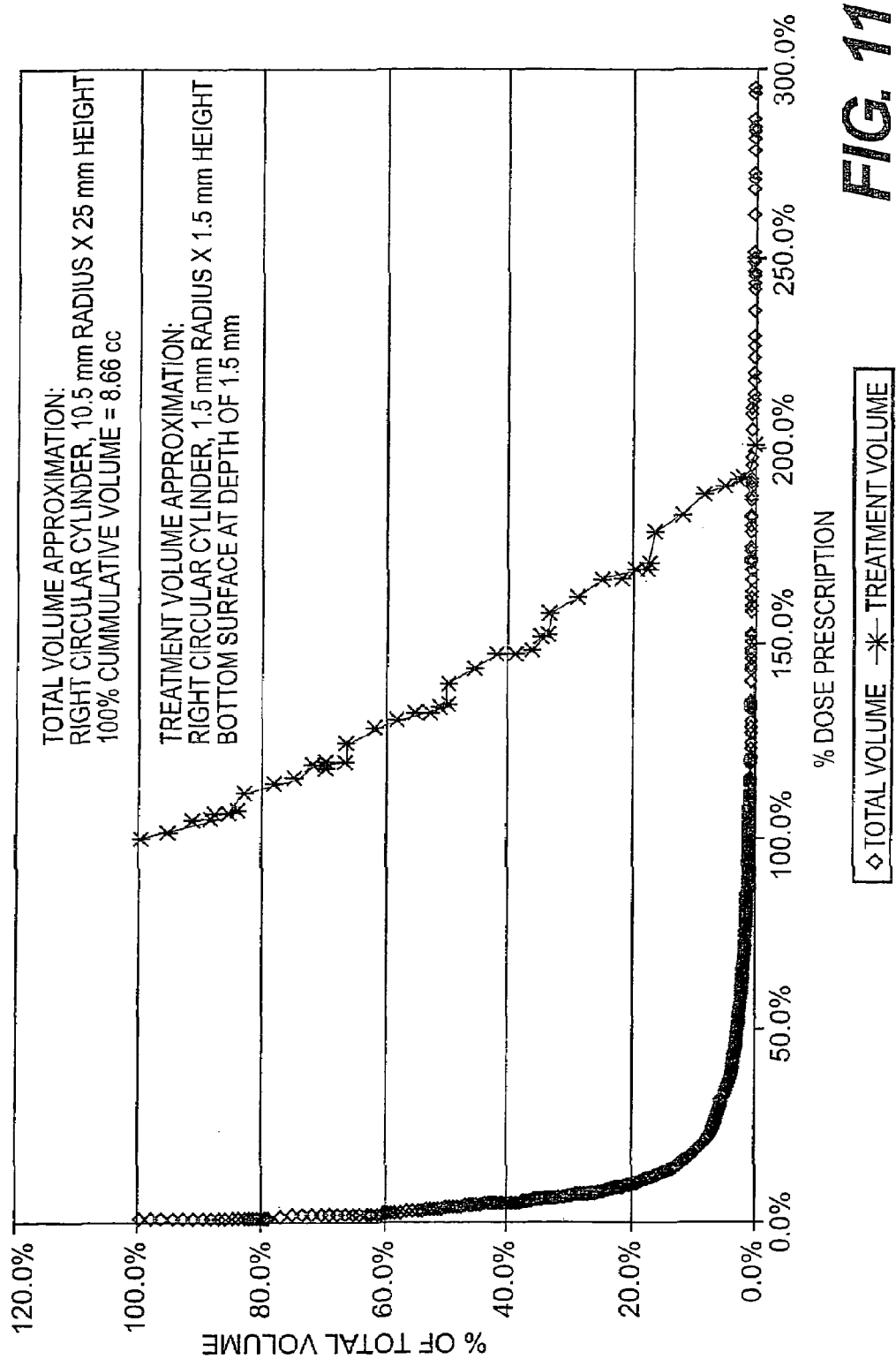
FIG. 11 is a dose volume histogram (DVH) for a cylindrical approximation of the volume of an eye.

FIG. 8 exemplifies a dose rate profile of a brachytherapy device in accordance with the present invention at points where the radial distances (r), as defined in FIG. 5, are 0 mm and 1.5 mm, respectively and the axial distance (z), as defined in FIG. 5, is 0–20 mm. FIG. 9 is a plot of the isodose curves of a brachytherapy device according to the present invention. FIG. 10 is a plot of the isodose curves of a brachytherapy device according to the present invention with a wider axial and radial range than the device used to generate the plot of FIG. 9. FIG. 11 is a dose volume histogram (DVH) for a cylindrical approximation of the volume of an eye.

Figure 12:
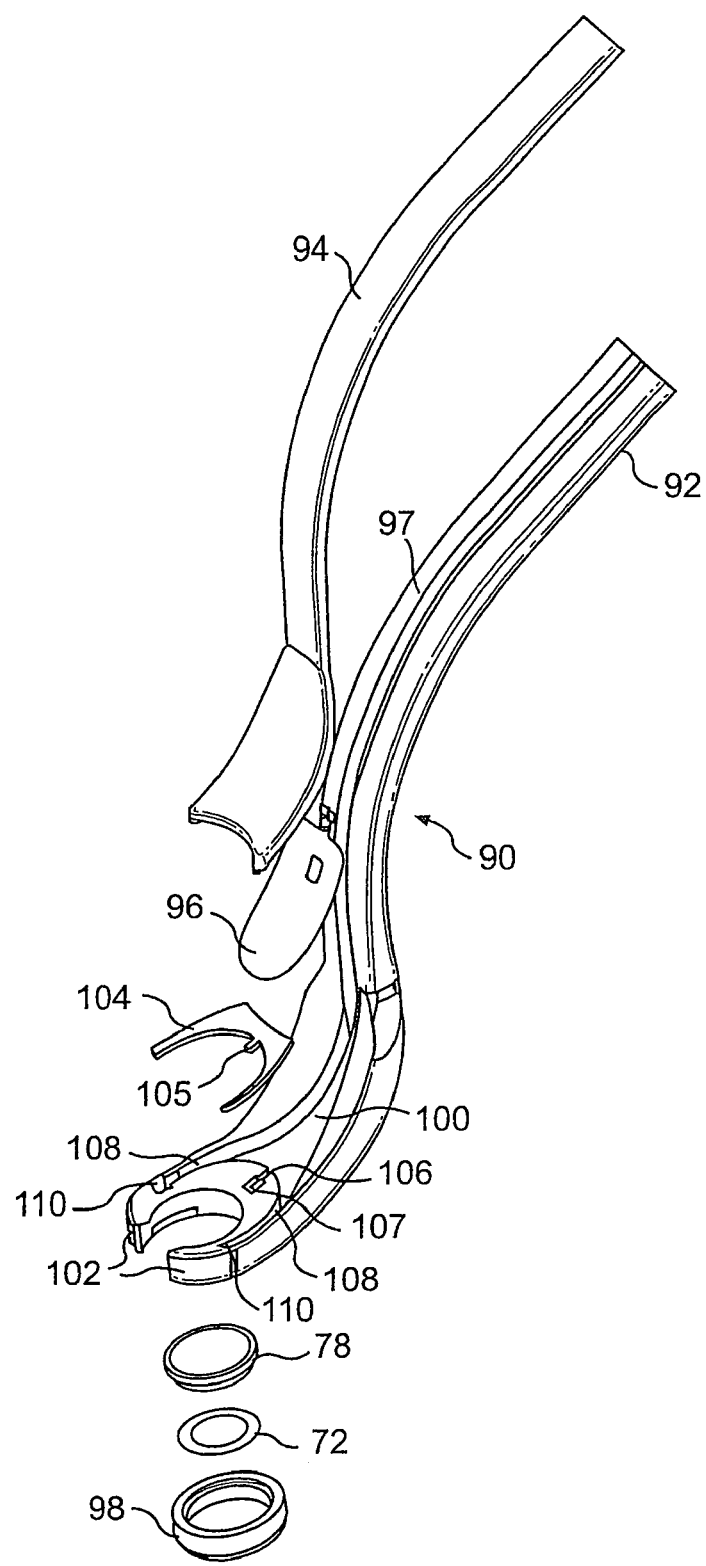
FIG. 12 is an exploded view of one embodiment of a wand and holder in accordance with the present invention.

FIG. 12 is an exploded view of one embodiment of a wand 90 in accordance with the invention. Wand 90 includes a wand body 92 for housing the holder 98, and the retractable shield 96. Wand body 92 is provided with a cover 94 for covering over the retractable shield 96. Cover 94 may be attached to wand body 92 by any suitable means such as a snap fit. The wand body 92 also includes a groove 100 in which retractable shield 96 and shield connector 97 are housed in a manner, which permits sliding movement of retractable shield 96 and shield connector 97 within the groove 100 to permit retraction of the retractable shield 96 in use. Wand body 92 also includes a pair of arms 102 at the distal end thereof between which holder 98 fits. Holder 98 is positioned in slot 102 with annular ring 72 and cap 78 located therein.

Optionally, wand body 92 may be provided with an optics cover 104, which includes a tab 105 designed to fit into slot 106 in wand body 92. Tab 105 has, for its purpose to cover illumination point 107 when optics cover 104 is in the closed position. Shield 96 includes a hole 95 therein which can permit light from illumination point 107 to pass through. In one embodiment, hole 95 has a filter that changes the color of the light from illumination point 107 such that the physician knows by the light color if the shield 96 is retracted or not. This gives the physician a third illumination point 107 to use for positioning the device, as well as an indicator to remind the physician about the position of the retractable shield. Wand body 92 may also include channels 108 for the provision of fiber optic or light pipe illumination via illumination ports 110 located on either side of the holder 98 on the distal end of the wand body 92.

Figure 13:
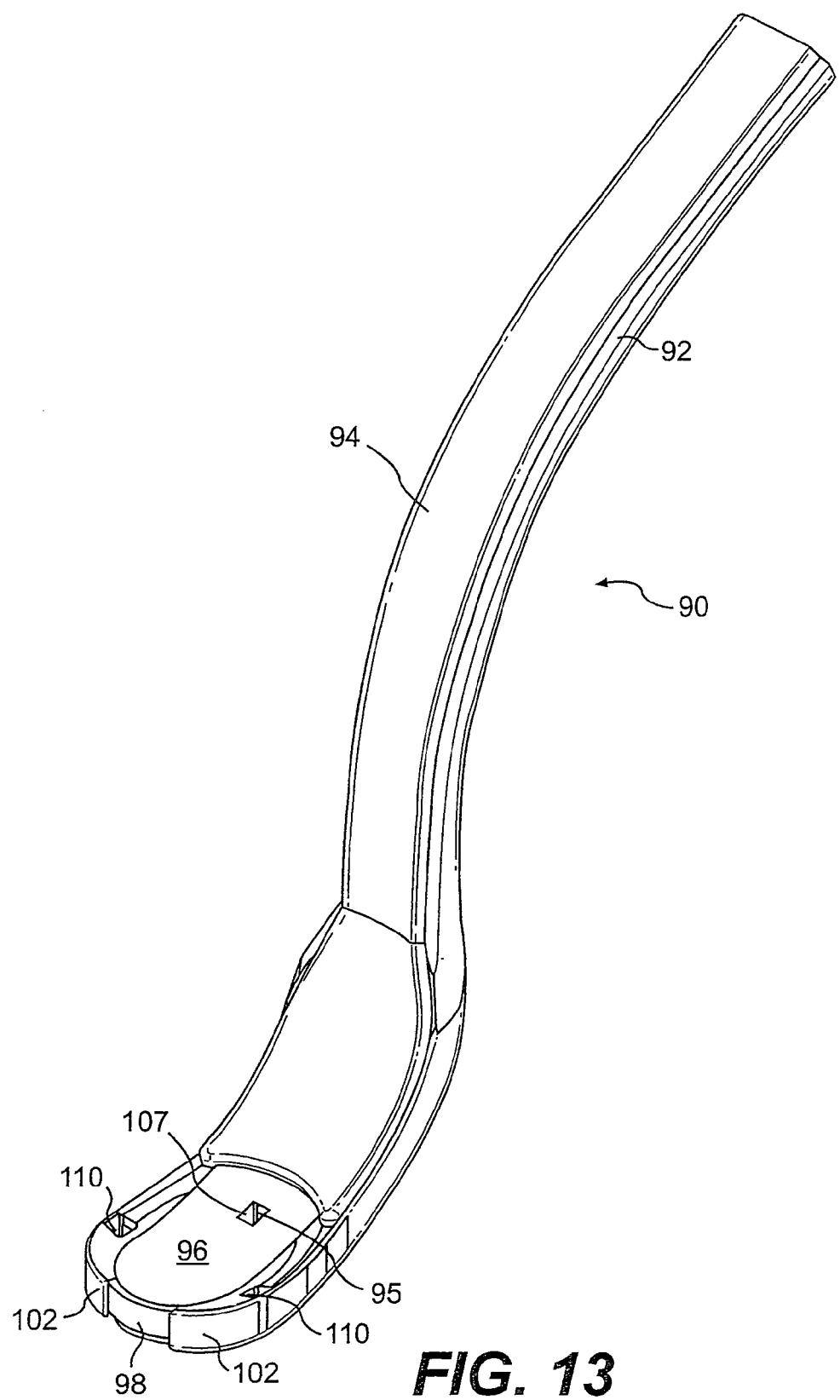
FIG. 13 is a perspective view of the wand and holder of FIG. 12 with the shield located in the closed position.

Referring to FIG. 13, wand 90 is shown with the retractable shield 96 and cover 94 in the closed positions. The wand 90 is inserted into the eye of the patient in this configuration and is also removed from the eye of the patient in this configuration.

Figure 14:
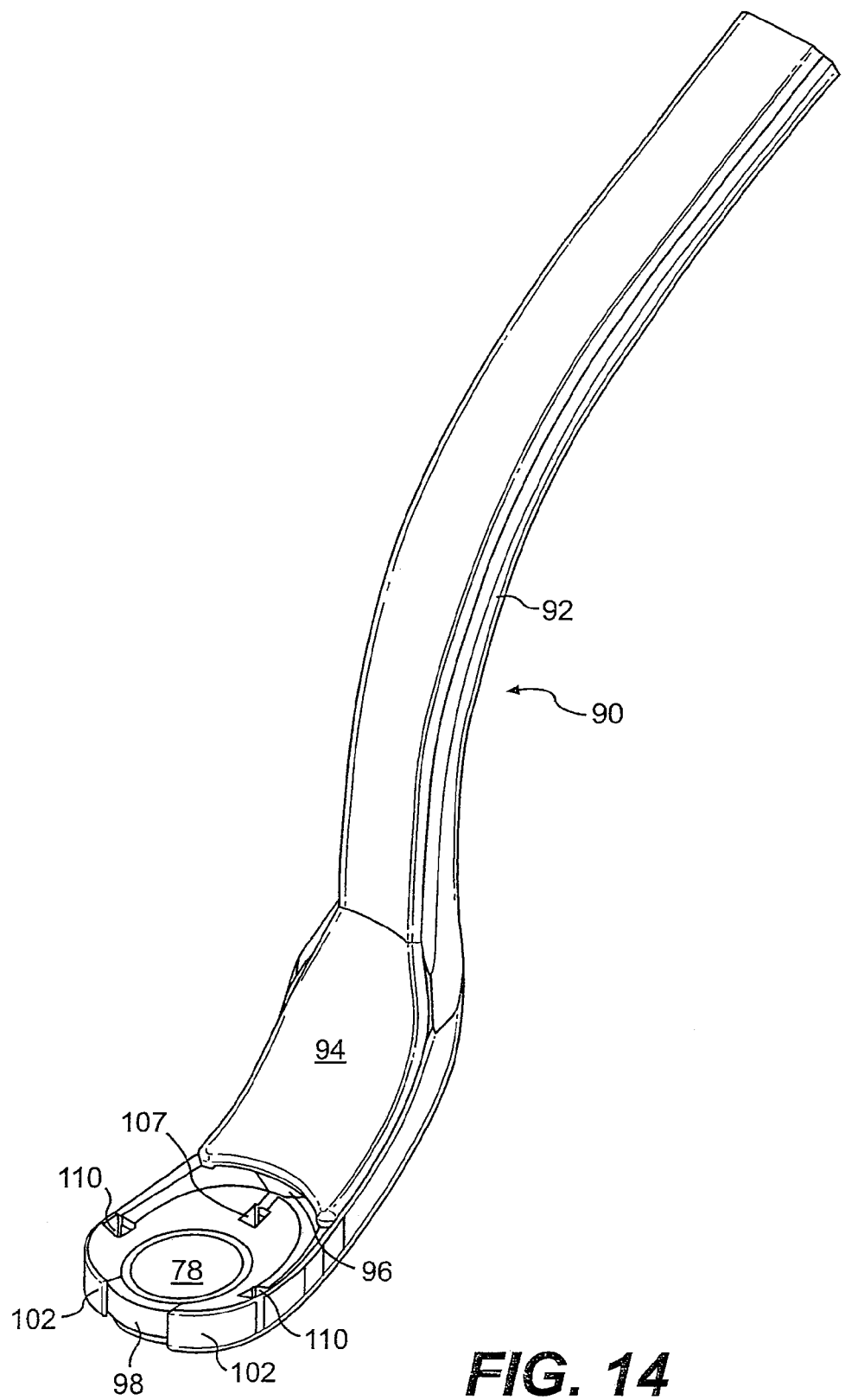
FIG. 14 is a perspective view of the wand and holder of FIG. 12 with the shield located in the open position.

Referring to FIG. 14, wand 90 is shown with the retractable shield 96 in the retracted position. In this position, illumination points 107 and 110 are clearly visible and cap 78 and the radioactive material thereunder is exposed to permit irradiation of the patient. This is the position of the wand 90 during treatment of the patient.

Figure 15:
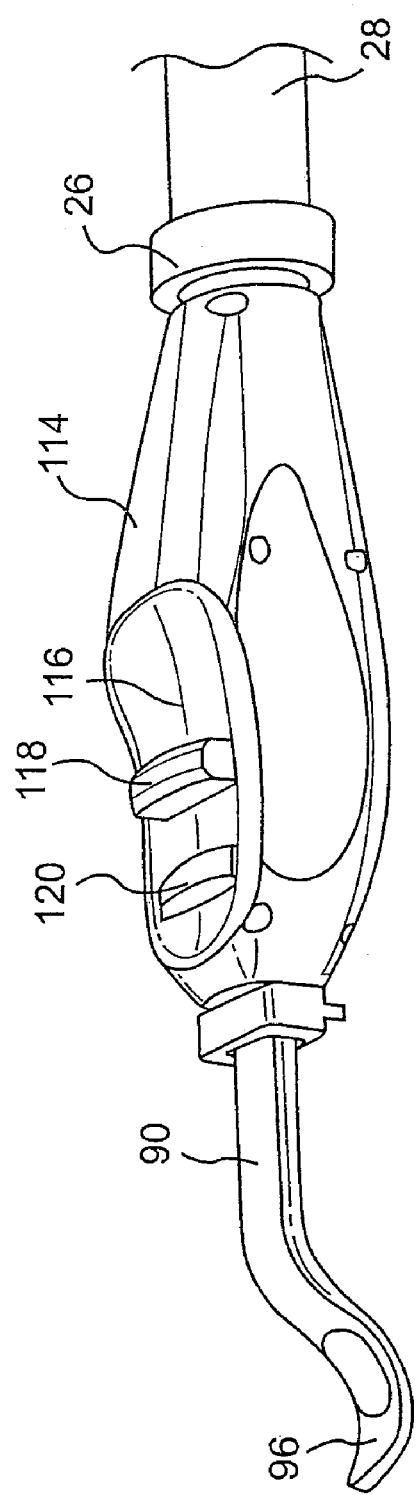
FIG. 15 is a perspective view of one embodiment of a handle fitted with a wand and holder of the present invention.

Referring to FIG. 15, there is shown another embodiment of a wand handle 114 in accordance with the present invention. Wand handle 114 is preferably shaped to provide easy gripping by the physician, for example, as shown in FIG. 15. Wand handle 114 includes an actuator slot 116 and a shield actuator 118 for retracting and closing the shield 96. Shield actuator 118 is connected to shield connector 97 such that when the physician pulls shield actuator 118 back in actuator slot 116 away from the distal end of the device, shield 96 is retracted to the position shown in FIG. 14. Conversely, when the physician pushes shield actuator 118 in actuator slot 116 forward towards the distal end of the device, the shield 96 is closed over the radioactive material as shown in FIG. 13. Wand handle 114 may also include a locking channel 120 sized to fit and hold shield actuator 118 at a location whereby shield 96 is in the closed position.

Figure 16:
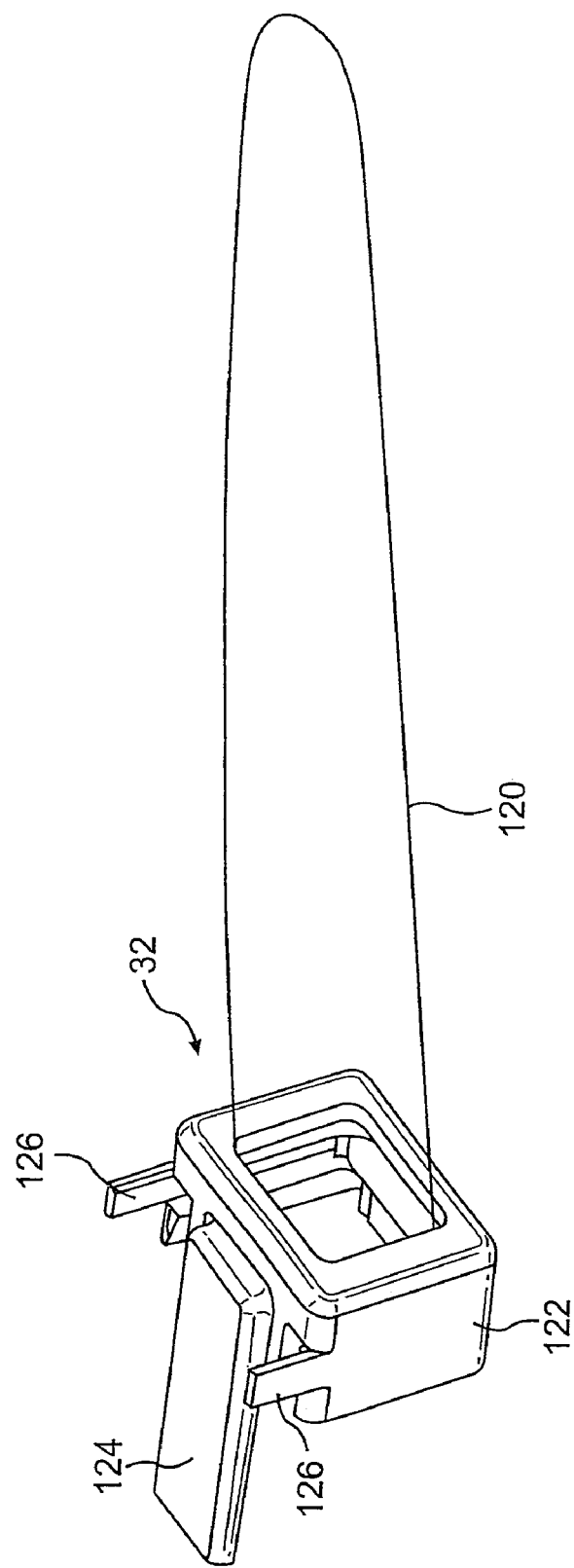
FIG. 16 is a perspective view of a sheath in accordance with one embodiment of the present invention.

FIG. 16 shows a perspective view of a disposable sheath 32 in accordance with the present invention. Disposable sheath 32 includes a transparent sheath portion 120, which is preferably sterile. Sheath portion 120 is connected to a sheath ring 122, which provides structural support and acts as a base for sheath portion 120. Sheath ring 122 is preferably provided with a key 124 or other, similar device for unlocking the retractable shield 96 of the wand 90. This will prevent the physician from inadvertently retracting the shield 96 without having a sterile sheath 32 attached to the device since the retractable shield 96 will not function unless the key 124 is inserted into the device. Sheath ring 122 may also be provided with a pair of tear off tabs 126 which hold sheath ring 122 in wand 90 but can be torn off to remove sheath ring 122 from wand 90. In this manner, reuse of a sheath 32 can be prevented since, after one use, the tear off tabs 126 will have been removed.

Figure 17:
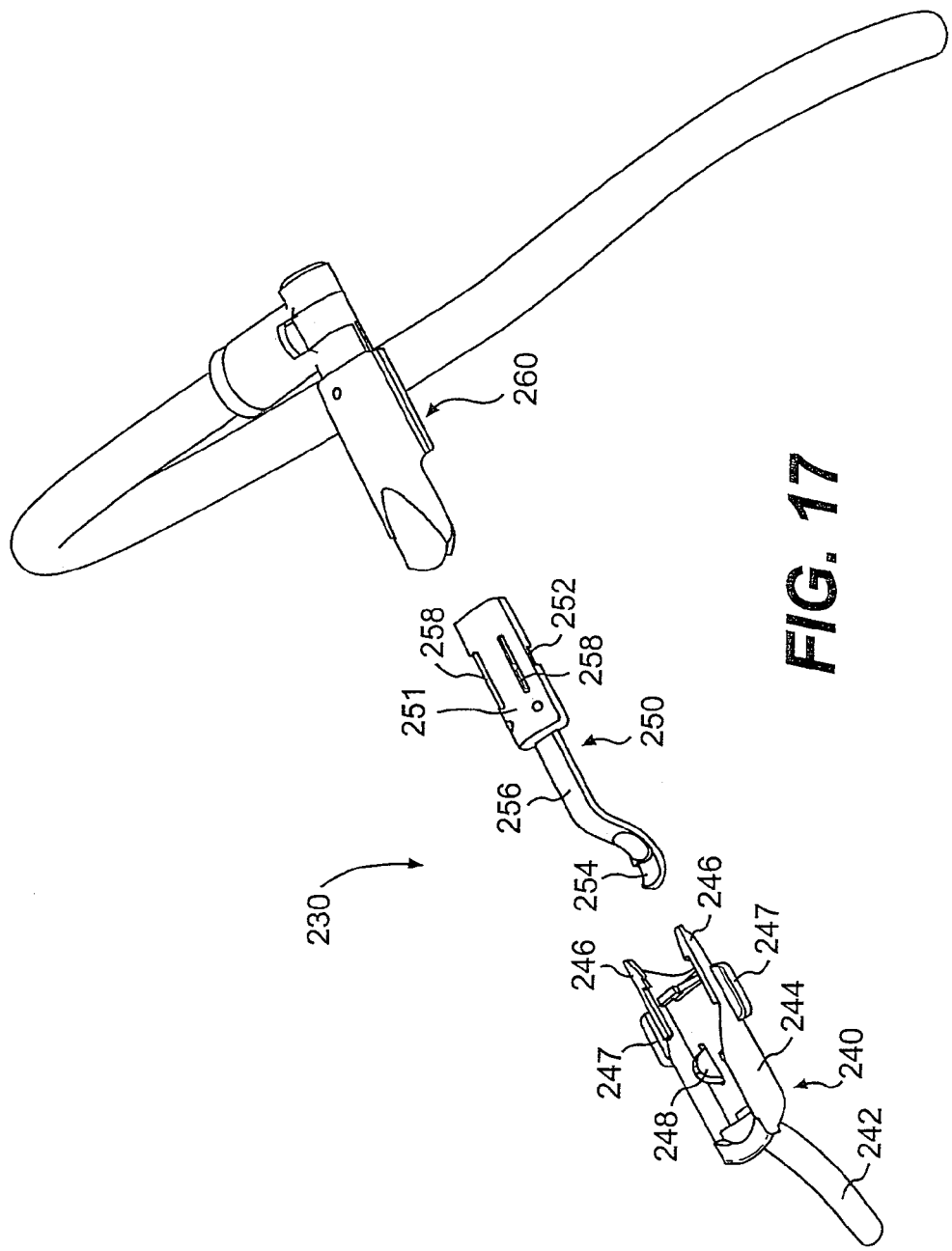
FIG. 17 is a perspective view of another alternative embodiment of a brachytherapy device in accordance with the present invention with the three components disassembled.

Referring to FIG. 17, there is shown another, more preferred alternative design of a brachytherapy device 230 in accordance with the present invention. In this embodiment, brachytherapy device 230 is made up of three components, the disposable sheath and housing 240, the source and shielding mechanism 250 and the articulating arm 260.

The disposable sheath and housing 240 includes a disposable sheath 242 attached to a housing 244. The disposable sheath and housing 240 snap onto the source and shielding mechanism 250 via tabs 246 that snap into slots 252 on source and shielding mechanism 250. Disposable sheath and housing 240 also includes an actuating device 247 attached to a shield retracting mechanism 248 that engages with a shield-retracting device located within source and shielding mechanism 250. One advantage of this arrangement is that since integral parts of the shield-retracting device are located in two different components of the brachytherapy device 230, the device 230 cannot be used without both of these components being present. As a result, this design necessitates the use of the disposable sheath and housing 240 to thereby prevent a physician from employing the device without a sterile sheath 242 attached thereto.

Source and shielding mechanism 250 also include a housing 251 that houses a portion of the shield-retracting mechanism, not shown. Source and shielding mechanism 250 also includes a wand 256 and a shield 254. Slots 258 in source and shielding mechanism 250 are provided to engage with a releasable connecting device, not shown, which forms part of articulating arm 260 for releasably connecting source and shielding mechanism 250 to articulating arm 260.

Figure 18:
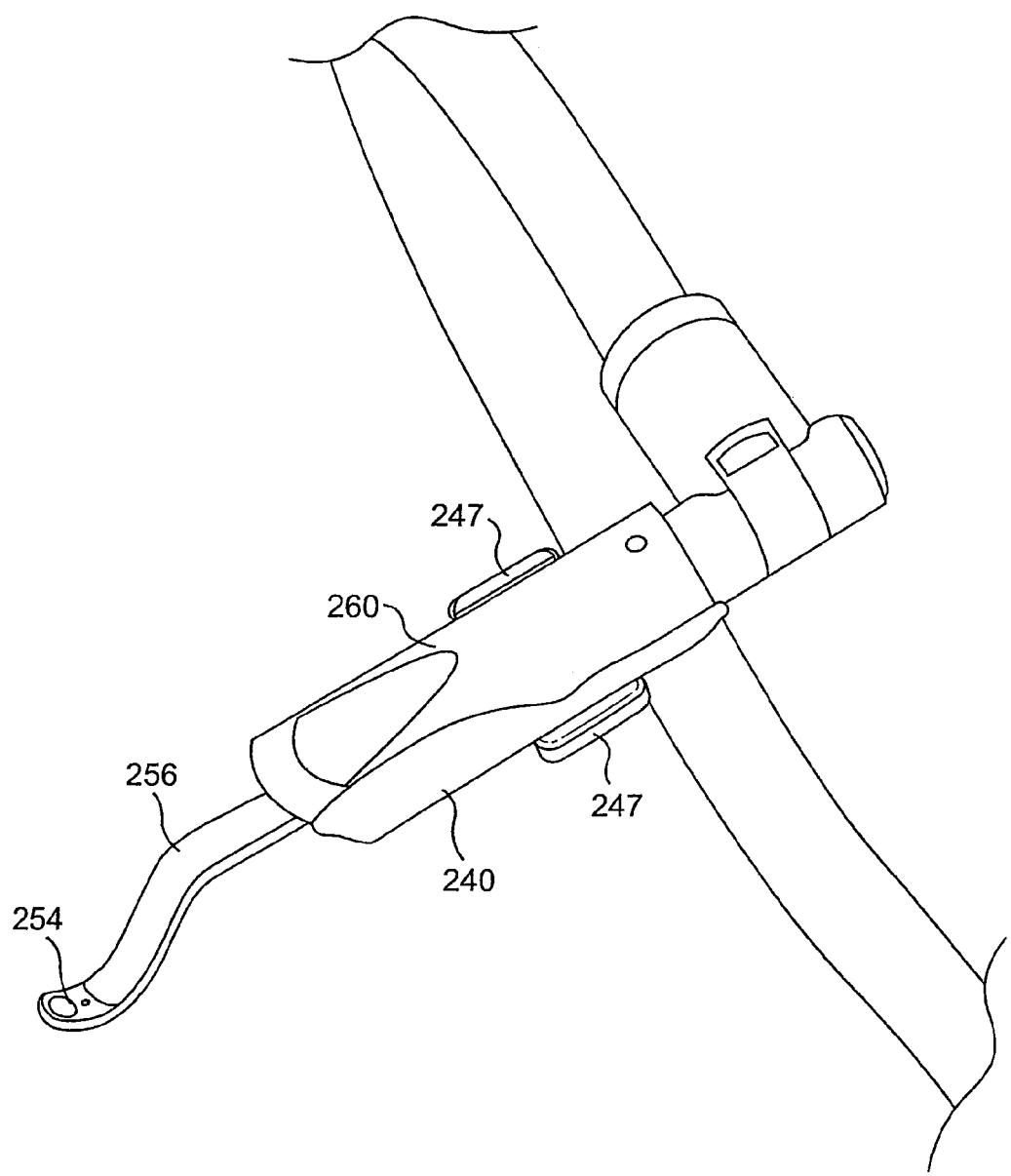
FIG. 18 is a perspective view of the assembled device of FIG. 17 with the shield extended.
Figure 19:
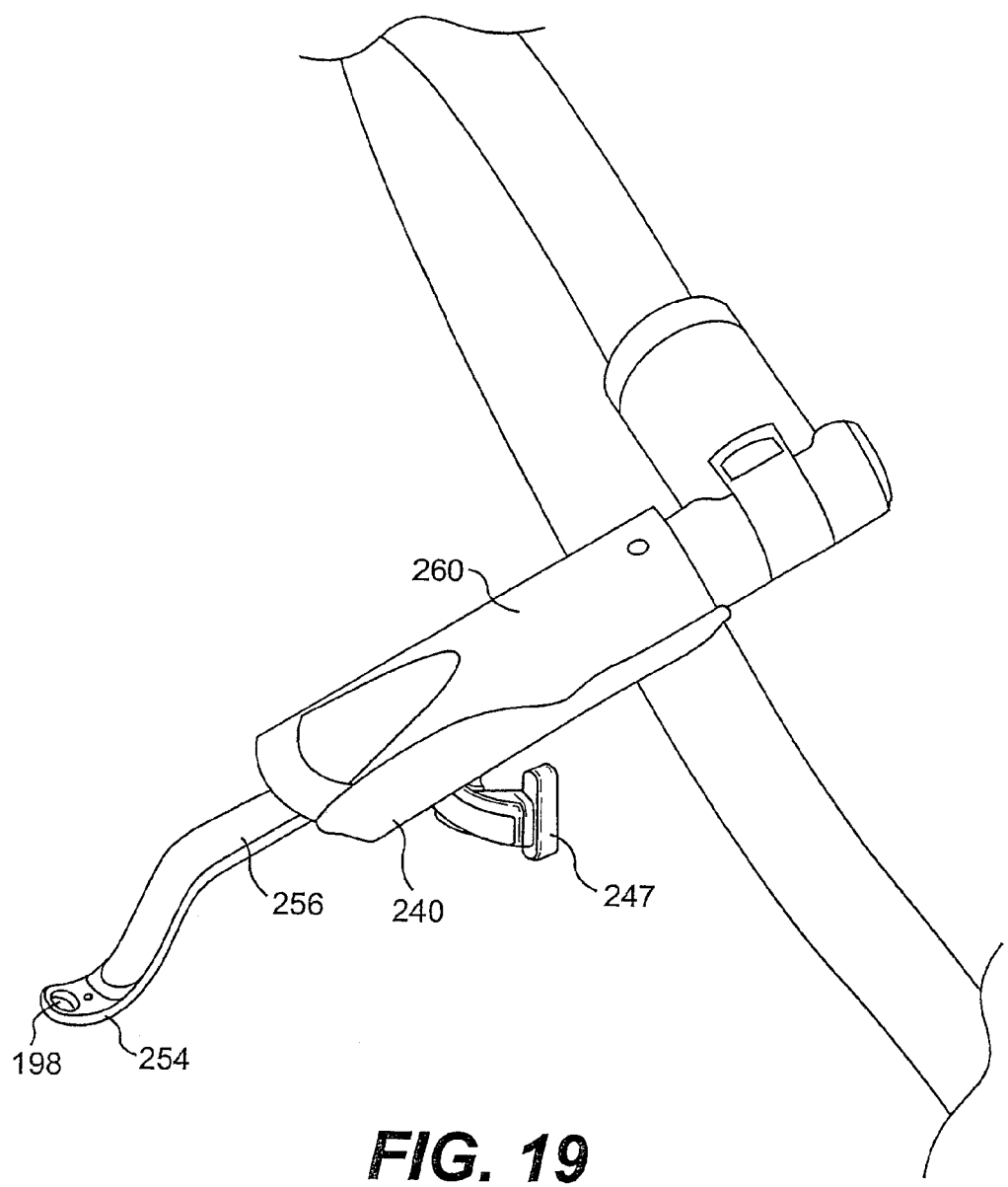
FIG. 19 is a perspective view of the assembled device of FIG. 17 with the shield retracted.

FIG. 18 shows the device of FIG. 17 with the shield 254 extended to cover the radioactive material, as it would be during insertion and removal of the device from the patient. FIG. 19 shows the device of FIG. 17 with the shield 254 retracted to expose the holder 198 containing the radioactive material, as the device 230 would be during treatment of the patient. The position of actuating device 247 is shown in FIG. 19 and the device 230 has been specially designed such that the actuating device 247 is in a noticeable position when the shield 254 is retracted to help prevent the physician from trying to remove the device 230 from a patient with the shield 254 in the retracted position. In fact, the position of the actuating device with the shield 254 retracted is inconvenient for removal of the device 230 from the patient to thereby discourage removal with the shield 254 in the retracted position.

The invention will be further illustrated with reference the following example, which is not to be construed as limiting the scope of the invention in any way.

EXAMPLE

To further demonstrate effectiveness of the brachytherapy device of the present invention for delivering a substantially uniform dose rate profile, a dose rate profile of one embodiment of the holder 130 as shown in FIG. 5 is given below.

In the device of FIG. 5, the gold ring 142 has an outer diameter of 5 mm and inner diameter of 3.5 mm and is plated with about 90 μg of nearly carrier free palladium-103. The back of the gold ring 142 has previously been provided with a masking material that prevents plating of the bottom surface of the gold ring 142. The nominal radioactivity of the radioactive material employed for this example is about 3 Ci. The bottom 146 and sidewall 144 are both made from 316 stainless steel. The cap 148 is made from polysulfone, which also provides some "stand-off" from the radioactive material to the upper surface 149 of the cap 148. This "stand-off" helps to prevent the low-energy L x-rays emitted by the radioactive material from delivering a high surface dose rate.

The dose rate profile can be measured with specialized ion-chambers such as an extrapolation chamber. Alternatively, Thermoluminescent Dosimeters (TLDs) can also be used to measure the dose rate profile of the radioactive material used in the invention. However, it is difficult to perform these measurements and are typically associated with large measurement uncertainties. An accepted alternative to such experimental measurements, is a method of determining the dose rate profile is using mathematical modeling, specifically, Monte Carlo analysis via a suitable computer program such as MCNP (version 4C) (see J. Briesmeister, "MCNP-A General Monte Carlo N-Particle Transport Code," Los Alamos National Laboratory, LA-1309-M, Version 4C, March 2000, which is incorporated by reference herein for its disclosure of the MCNP version 4C code). Monte Carlo analysis is well known to a skilled artisan and is disclosed by many publications such as J. Williamson, "Comparison of measured and calculated dose rates in water near I-125 and Ir-192 seeds," Med. Phys. 18(4), July/August 1991; and M. Napolitano, "Dosimetric Characterization for Pd-103 Direct Coated Nitinol Wire Intravascular Brachytherapy Source Design DC-1," MN-01-003-TR, May 7, 2001, which are incorporated by reference herein for their disclosures of the use of the Monte Carlo method for modeling dose rate profiles for radioactive materials. The following results on the dose rate profile of the brachytherapy device described above are derived from Monte Carlo analysis.

The results form the dose rate calculations represent the dose rate, in a fixed geometry, at a fixed point, from a source of unit activity. The units for the dose rate constant are dose per unit time per unit activity, or more commonly, cGy-mCi$^{-1}$-hr$^{-1}$ or Gy-Ci$^{-1}$-min$^{-1}$. This value must be combined with the activity of a radioactive material to determine the dose rate for the specific radioactive material.

Two approaches to the dose-rate calculation have been used, both of which are done in water. The first approach calculates the dose-rate with surface tallies at various heights (or axial distance) above the upper surface 149 of the cap 148. A series of planar surfaces of the water are segmented with concentric cylinders to calculate the dose rate at various radii. The second approach is to use volume tallies. Again, the water above the device is segmented with several planes and concentric cylinders, but instead of calculating the dose-rate at each surface, the dose-rate is calculated in each volume. These volume calculations are used to develop a simplified dose-volume histogram. Both of these approaches take advantage of the cylindrical symmetry of the device.

The parameters used in the calculation for each material used in the brachytherapy device are listed in Table 1 below.

TABLE 1

| Material | Density (g/cm3) | Element | Weight % |
|---|---|---|---|
| 316-Stainless Steel | 7.92 | Fe | 65.5 |
| | | Cr | 17.0 |
| | | Ni | 12.0 |
| | | Mo | 2.5 |
| | | Mn | 2.0 |
| | | Si | 1.0 |
| Polysulfone | 1.24 | C | 73.3 |
| | | H | 4.98 |
| | | S | 7.24 |
| | | O | 14.5 |
| Gold | 19.32 | Au | 100 |
| Palladium | 12.0 | Pd | 100 |
| Polyimide | 1.1 | C | 72.06 |
| | | H | 11.57 |
| | | N | 7.64 |
| | | O | 8.73 |
| Water | 1.0 | O | 88.8099 |
| | | H | 11.1901 |

The $^{103}$Pd emitted radiation energy spectrum was taken from "Table of Radioactive Isotopes," Virginia Shirley, editor, 1986 edition, page 103-2 and is shown in Table 2 below. The $^{103}$Pd is uniformly plated on the gold ring 52 with an average thickness of 0.75 μm.

TABLE 2

| Energy (MeV) | Emission Probability | Percent of Total |
|---|---|---|
| 0.002377 | 0.0017 | 1.99E-01 |
| 0.002519 | 0.0009 | 1.06E-01 |
| 0.002696 | 0.046 | 5.40E+00 |
| 0.002833 | 0.03 | 3.52E+00 |
| 0.003179 | 0.0025 | 2.93E-01 |
| 0.020074 | 0.223 | 2.62E+01 |
| 0.020216 | 0.424 | 4.97E+01 |
| 0.022717 | 0.104 | 1.22E+01 |
| 0.023312 | 0.0194 | 2.28E+00 |
| 0.039755 | 0.000683 | 8.01E-02 |
| 0.053277 | 3E-07 | 3.52E-05 |
| 0.06251 | 1.04E-05 | 1.22E-03 |
| 0.24186 | 6.7E-09 | 7.86E-07 |

TABLE 2-continued

| Energy (MeV) | Emission Probability | Percent of Total |
|---|---|---|
| 0.29495 | 0.000028 | 3.28E-03 |
| 0.3177 | 1.5E-07 | 1.76E-05 |
| 0.35746 | 0.000221 | 2.59E-02 |
| 0.443777 | 1.47E-07 | 1.72E-05 |
| 0.497054 | 4.01E-05 | 4.70E-03 |
| Total | 0.852483 | 100.00 |
| Total (>20 keV) | 0.7714 | 90.49 |
| Total (7-37 keV) | 0.7704 | 90.37 |

Surface (F2) Tally Calculations in Water

The MCNP model used to determine the dose rate consists of the holder 68 together with radioactive material and the cap 148 suspended in a 30 cm diameter sphere of liquid water. A mathematical representation of the geometry of the radioactive material together with the holder 130 and the cap 148, including the multiple layers of material and accurate physical dimensions, is suspended in the center of the sphere. A series of planes are set at axial dimensions from z=0–20 mm, where z is measured axially from the upper surface 149 of the cap 148. A series of concentric cylinders are introduced to segment the planes with radii ranging from r=0–20 mm, where r is measured from the center of the radioactive material. The model calculates the radiation flux crossing the individual annuli and the corresponding dose rate per unit activity. The planar surfaces are infinitely thin, but the segmentation has a specific width. The dose rate is assigned to the midpoint between the inner and outer radii of the segment.

The result of the F2 tally is fluence, in particles per unit area per initial photon. The amount of energy deposited by these particles is calculated within the model by means of the following equation:

$$D = C_1 \Phi \sigma_{total} H;$$

Wherein:
D=Dose Rate Constant (Gy/Ci-min)
$C_1$=Conversion Factor
Φ=Particle Fluence (#/cm$^2$)
$\sigma_{total}$=Total Cross-section (barns/atom)
H=Photon Heating (MeV/Collision)

The conversion factor C1 is a function of material (liquid water) properties, the radioactive material ($^{103}$Pd) properties, and unit conversions.

In this case, $C_1$=30.40(Gy-cm$^2$)/(barn-MeV-Ci-min)

The result of the surface tally calculations is a series of data points at various axial and radial distances. The targeted treatment point (also called prescription point) is at r=0 and z=3.0, where z is measured from the upper surface 149 of the cap 148. The dose rate at the prescription point is 0.64 Gy-Ci$^{-1}$-min$^{-1}$. The difference in the shapes of the axial dose rate profile at r=0 mm and r=1.5 mm are shown in FIG. 8. The radius of 1.5 mm represents the area directly over the active portion of the radioactive material, while the center axis is not directly above the radioactive material since the center axis is located within the annulus formed by the radioactive material. Even though FIG. 8 shows that the centerline profile (r=0 mm) is initially depressed, at the prescription depth of 3 mm, both profiles are very similar. As a result, the dose rate profile of the holder 130 together with the radioactive material and the cap 148 is substantially uniform over the treatment area, as desired.

A more complete picture of the dose rate profile of the holder 130 together with the radioactive material and the cap 148 calculated by the surface tally model is shown in FIG. 9. The array of data derived from the modeling was further processed using data analysis software, and an isodose contour plot was developed. The curves represent lines of constant dose rate and are labeled as the percent of the prescription or therapeutic dose (a desired dose to be applied to the treatment area at a given prescription depth). The prescription depth is noted by a line at the 3.0 mm mark (hereafter "prescription line"). The width of the prescription line is about 5 mm to represent the diameter of the holder 130. Note that the diameter of the area of the 90% of prescription dose rate contour line is slightly further away from the contact surface of the holder 130 than the prescription line. Therefore, a dose rate of at least 90% of the prescription dose rate will be delivered at most locations within the prescription line. As further shown by FIG. 9, at least 80% of the prescription dose rate is delivered to a spot within the full 5 mm in diameter from the centerline (r=0) and within the prescription line.

FIG. 10 shows the same contour plot with a wider axial and radial range. There is a rapid drop off of the dose curves outside the treatment area. For example, at a radial distance of 10 mm, the dose rate has dropped to approximately 1% of the prescription dose. This represents the unwanted dose delivered to, for example, the optic nerve during treatment of macular degeneration, and should represent an acceptable delivered dose outside the treatment area.

Volume (F4) Tally Calculations in Water

The volume tally model is set up in a similar configuration as for surface tallies. A series of planes are set at axial dimensions from z=0–25 mm, where z is measured axially from the upper surface 149 of the cap 148. A series of concentric cylinders are introduced to segment the planes with radii ranging from r=0–20 mm, where r is measured from the center of the annular ring 142 coated with the radioactive material.

The dose rate calculated with the F4 tally is a measure of the average across a cell. Therefore, the cells close to the upper surface 149 of the cap 148 must be small to minimized variations due to dose rate changes as a function of depth. As a result, individual annular volumes range from 0.25 mm in depth close to the device, to a few mm in depth further away. The code calculates the average energy dependant fluence through each volume and uses the same tally multiplier as described in the Surface Tally Calculation method to convert to dose rate. Finally, the average dose rate to the cell is assigned to the geometric centroid of the cell.

A dose volume histogram (DVH) is a measure of what volume of tissue receives a particular level of dose. The volume tally data from the modeling was used to develop a simplified DVH for the holder 130 together with the radioactive material and the cap 148.

To mimic the volume of an eye, which is approximately a 25 mm diameter sphere, a right annular cylinder 10.5 mm in radius and 25 mm high was used. The total volume of the cylinder is 8.66 $cm^3$, while the volume of a 25 mm sphere is 8.18 $cm^3$. The target volume for the treatment of macular degeneration will vary and may require different sizes of the holder 130 material. The 5 mm diameter holder 130 was designed to treat an idealized volume consisting of a thin right annular cylinder, 3 mm in diameter located at a depth of 1.5–3.0 mm. The total volume of this idealized treatment area is 0.011 $cm^3$, or 0.13% of volume of the cylindrical model approximation of the eye.

The volume of each cell in the model was calculated and paired with the dose rate delivered. As noted above, the dose rate to the prescription point is 0.64 Gy-$Ci^{-1}$-$min^{-1}$. The dose to each volume was normalized by dividing by the prescription dose rate and multiplied by 100 so the normalization could be represented by a percentage. The data was sorted in descending order such that the volume receiving the highest dose rate was first. The cumulative volume was incrementally calculated, as a function of decreasing dose rate to the volume. The cumulative volume was normalized to the entire volume of the eye. The result is shown in FIG. 11. As can be seen in the graph, less than 2% of the entire volume receives a dose rate greater than the prescription dose rate, and 90% of the entire volume received less than 20% of the prescription dose rate. In addition, the dose rate distribution to the treatment area is also shown. The volume curve shows that 100% of the treatment area receives at least 100% of the prescription dose. Only approximately 35% of the treatment area receives a dose of 150% or greater, and no part of the treatment area receives greater than 200% of the prescription dose.

Accordingly, the brachytherapy device of the invention achieves one objective of the invention, which is to shape the dose rate profile to maximize the dose delivered to the target tissue of the eye and minimize the dose delivered to non-target tissue of the eye.

It is to be understood that the scope of the invention is to be determined from the claims appended hereto.

What is claimed is:

1. A brachytherapy device comprising:
   a holder formed by a bottom and an annular sidewall affixed at a first end to said bottom to define a cavity within said holder, said holder having an opening at a second end of said annular sidewall;
   a radioactive material located within the cavity of said holder of said brachytherapy device, said radioactive material having a generally annular shape and which delivers a dose rate of about 0.01 to about 10.0 Gy-$min^{-1}$, and
   said sidewall and bottom comprising a sufficient amount of a radiation shielding material to shield a substantial amount of the radiation emitted by said radioactive material of said brachytherapy device.

2. A brachytherapy device as claimed in claim 1, further comprising a cap positioned in said cavity such that at least a portion of said cap is located between said radioactive material and the opening in the holder at the second end of the annular sidewall.

3. A brachytherapy device as claimed in claim 2, wherein said cap is retained within said sidewall be a device selected from the group consisting of a snap fit, a slip fit, a friction fit, a threaded fit, a mechanical fastener and combinations thereof.

4. A brachytherapy device as claimed in claim 3, wherein at least the portion of the cap located between the radioactive material and the opening is made from a radiation-transmitting material.

5. A brachytherapy device as claimed in claim 4, wherein at least the portion of the cap located between the radioactive material and the opening is made from a radiation-transmitting material that at least partially shields low energy x-ray radiation and transmits other radiation emitted by said radioactive material.

6. A brachytherapy device as claimed in claim 5, wherein the thickness of the portion of the cap located between the radioactive material and the opening is sufficient to prevent substantially all of the radiation emitted by the radioactive material from reaching said opening.

7. A brachytherapy device as claimed in claim 3, wherein the mechanical fastener comprises a peripheral lip attached to said sidewall around said opening.

8. A brachytherapy device as claimed in claim 1, wherein said substantially cylindrical cavity has a diameter of less than 15 mm, and a height of less than 3 mm.

9. A brachytherapy device as claimed in claim 1, wherein said annular radioactive structure of said brachytherapy device is affixed to the bottom of said holder.

10. A brachytherapy device comprising:
a handle,
a wand that is releasably attachable to said handle at a proximal end of said wand,
a holder located at a distal end of said wand, said holder being formed by a bottom and an annular sidewall affixed at a first end to said bottom to define a cavity within said holder, said holder having an opening at a second end of said annular sidewall;
a radioactive material located within said cavity and which delivers a dose rate of about 0.01 to about 10.0 Gy·min$^{-1}$, and
a cap positioned in said cavity such that at least a portion of said cap is located between said radioactive material and the opening in the holder at the second end of the annular sidewall,
said annular sidewall and said bottom comprising a radiation-shielding material that shields a substantial portion of the radiation emitted by said radioactive material; and
said radioactive material and said holder cooperating to provide at least 90% of a prescription dose rate at a predetermined prescription depth from said radioactive material within a radius from a center of said radioactive material of at least about 1.3 times a radius of said radioactive material and a substantial reduction of the dose rate outside the treatment area.

11. A brachytherapy device as claimed in claim 10, further comprising a removable sheath covering at least the opening in said holder.

12. A radioactive therapeutic device as claimed in claim 10, wherein said radioactive material has an annular shape.

13. A radioactive therapeutic device as claimed in claim 10, wherein said radioactive material is attached to the bottom of said cavity.

14. A radioactive therapeutic device as claimed in claim 10, wherein said holder comprises a material selected from the group consisting of stainless steel, gold, tungsten, and lead.

15. A method for treating an eye by brachytherapy comprising the step of:
inserting a brachytherapy device containing a radioactive material between the sclera and the eyelid of said eye; and
exposing a portion of said eye located in a predetermined treatment area to radiation emitted from said brachytherapy device for a sufficient time to deliver a therapeutic dose of radiation at a dose rate of about 0.1 to about 10.0 Gy·min$^{-1}$ at a distance of about 3 millimeters from said surface of said brachytherapy device, and in a manner whereby a substantially uniform dose rate is delivered at a particular treatment depth to the portion of the eye located in the treatment area.

16. A method as claimed in claim 15, wherein a surface of said brachytherapy device through which said radiation is delivered to the treatment area, is positioned in contact with or in close proximity to the portion of the eye located in the treatment area.

17. A method as claimed in claim 16, wherein said brachytherapy device further comprises a shield that covers said surface, and the exposing step comprises the step of displacing said shield.

18. A method as claimed in claim 15, wherein said radioactive material has a radioactivity of about 0.1 to about 5 Ci.

19. A method as claimed in claim 18, wherein said radioactive material emits predominantly photon radiation.

20. A method as claimed in claim 19, wherein said photon radiation is selected from the group consisting of x-ray radiation, gamma-ray radiation and a combination thereof.

21. A method as claimed in claim 20, wherein said radioactive material comprises palladium-103.

22. A method as claimed in claim 15, wherein said brachytherapy device further comprises a radiation-transmitting cap, which forms at least a portion of said surface.

23. A method as claimed in claim 15, wherein the exposing step is carried out in a manner whereby there is a substantial reduction in the dose rate delivered outside the treatment area.

24. A method as claimed in claim 23, wherein the exposing step delivers a dose rate at a location in the treatment area at a predetermined treatment depth that varies by not more than 15% from the prescribed dose rate over the entire treatment area measured at said treatment depth.

25. A method as claimed in claim 24, wherein the exposing step delivers a dose rate at a radial distance from an outer edge of the treatment area of not more than one radius of the treatment area, and at a predetermined treatment depth, that is at least 33% less than the prescribed dose rate at said treatment depth, and the dose rate at a radial distance from the outer edge of the treatment area of not more that two radii of the treatment area and at a predetermined treatment depth is at least 60% less than the prescribed dose at said treatment depth.

26. A method as claimed in claim 25, wherein the dose rate varies by not more than 10% from the prescribed dose rate in said treatment area at said treatment depth.

27. A method as claimed in claim 26, wherein the dose rate delivered outside said treatment area at a radial distance from an outer edge of the treatment area of not more than one radius of the treatment area and at a predetermined depth is at least 50% less than the prescribed dose at said treatment depth, and the dose rate at a radial distance from the outer edge of the treatment area of not more than two radii of the treatment area and at a predetermined treatment depth is at least 75% less than the prescribed dose at said ,treatment depth.

28. A brachytherapy device comprising:
a handle,
a wand that is releasably attachable to said handle at a proximal end of said wand,
a holder located at a distal end of said wand, said holder being formed by a bottom and an annular sidewall affixed at a first end to said bottom to define a cavity within said holder, said holder having an opening at a second end of said annular sidewall;
a radioactive material located within said cavity and which delivers a dose rate of about 0.01 to about 10.0 Gy·min$^{-1}$,
a removable sheath covering at least the opening in said holder, said annular sidewall and said bottom comprising a radiation-shielding material that shields a substantial portion of the radiation emitted by said radioactive material; and said radioactive material and said holder cooperating to provide a substantially uniform dose rate of radiation at a predetermined treatment depth within a treatment area.

29. A radioactive therapeutic device as claimed in claim 28, wherein said radioactive material has an annular shape.

30. A radioactive therapeutic device as claimed in claim 28, wherein said radioactive material is attached to the bottom of said cavity.

31. A radioactive therapeutic device as claimed in claim 28, wherein said holder comprises a material selected from the group consisting of stainless steel, gold, tungsten, and lead.

* * * * *